(12) United States Patent
Sakaguchi

(10) Patent No.: US 8,345,957 B2
(45) Date of Patent: Jan. 1, 2013

(54) DATA PROCESSING APPARATUS, X-RAY APPARATUS, AND DATA PROCESSING METHOD

(75) Inventor: Takuya Sakaguchi, Shioya-gun (JP)

(73) Assignees: Kabushiki Kaisha Toshiba, Tokyo (JP); Toshiba Medical Systems Corporation, Tochigi-Ken (JP)

(*) Notice: Subject to any disclaimer, the term of this patent is extended or adjusted under 35 U.S.C. 154(b) by 810 days.

(21) Appl. No.: 12/367,913

(22) Filed: Feb. 9, 2009

(65) Prior Publication Data

US 2009/0207965 A1    Aug. 20, 2009

(30) Foreign Application Priority Data

Feb. 14, 2008 (JP) ................................ 2008-033360

(51) Int. Cl.
*G06K 9/00* (2006.01)
(52) U.S. Cl. ........................................................ 382/154
(58) Field of Classification Search .......... 382/131–132, 382/154, 305, 128; 345/419–420
See application file for complete search history.

(56) References Cited

U.S. PATENT DOCUMENTS

| | | | | |
|---|---|---|---|---|
| 5,283,837 | A * | 2/1994 | Wood | 382/285 |
| 6,424,731 | B1 | 7/2002 | Launay et al. | |
| 6,720,966 | B2 * | 4/2004 | Barth et al. | 345/424 |
| 7,050,844 | B2 * | 5/2006 | Strobel | 600/424 |
| 7,154,985 | B2 * | 12/2006 | Dobbs et al. | 378/4 |
| 7,197,170 | B2 | 3/2007 | Dwyer et al. | |
| 7,267,482 | B2 | 9/2007 | Ohishi | |
| 7,760,932 | B2 * | 7/2010 | Lee et al. | 382/154 |
| 7,869,646 | B2 * | 1/2011 | Park et al. | 382/154 |
| 7,889,902 | B2 * | 2/2011 | Zhang et al. | 382/128 |
| 2005/0197557 | A1 | 9/2005 | Strommer et al. | |
| 2006/0210019 | A1 * | 9/2006 | Rasche et al. | 378/62 |

FOREIGN PATENT DOCUMENTS

| | | |
|---|---|---|
| CN | 1691067 A | 11/2005 |
| JP | 2000-037376 A | 2/2000 |
| JP | 2002-119502 A | 4/2002 |
| JP | 2002-526188 A | 8/2002 |
| JP | 2004-178333 A | 6/2004 |
| JP | 2004-329729 A | 11/2004 |
| JP | 2006-187531 A | 7/2006 |
| JP | 2007-006913 A | 1/2007 |
| JP | 2007-020891 A | 2/2007 |
| JP | 2007-136164 A | 6/2007 |
| JP | 2007-528256 A | 10/2007 |
| JP | 2007-530122 A | 11/2007 |
| WO | 2008/001260 A2 | 1/2008 |
| WO | 2008/015611 A2 | 2/2008 |

OTHER PUBLICATIONS

Computer translation of Japanese Patent No. JP-178333, pp. 1-5.*

(Continued)

*Primary Examiner* — Daniel Mariam
(74) *Attorney, Agent, or Firm* — Yoshida & Associates, LLC

(57) ABSTRACT

An example of the present invention is a data processing apparatus including, a saving part configured to save three-dimensional data of a subject, a two-dimensional image display part configured to display three-dimensional data of the subject as a two-dimensional image, a designation part configured to designate coordinate information associated with a specific coordinate point on the two-dimensional image, a specifying part configured to specify, based on the coordinate information designated on the two-dimensional image, coordinate information on the corresponding three-dimensional data, and a calculation part configured to calculate a view angle of the subject on the basis of the coordinate information on the three-dimensional data.

15 Claims, 27 Drawing Sheets

OTHER PUBLICATIONS

U.S. Appl. No. 12/237,745, filed Sep. 25, 2008; Inventor: Takuya Sakaguchi.
U.S. Appl. No. 12/237,675, filed Sep. 25, 2008; Inventor: Takuya Sakaguchi.
Chinese Office Action dated Jun. 21, 2010 for related CN Application No. 200910007409.5.
English Translation of JP Office Action mailed on Jun. 19, 2012 for corresponding JP Application No. 2008-033360.

* cited by examiner

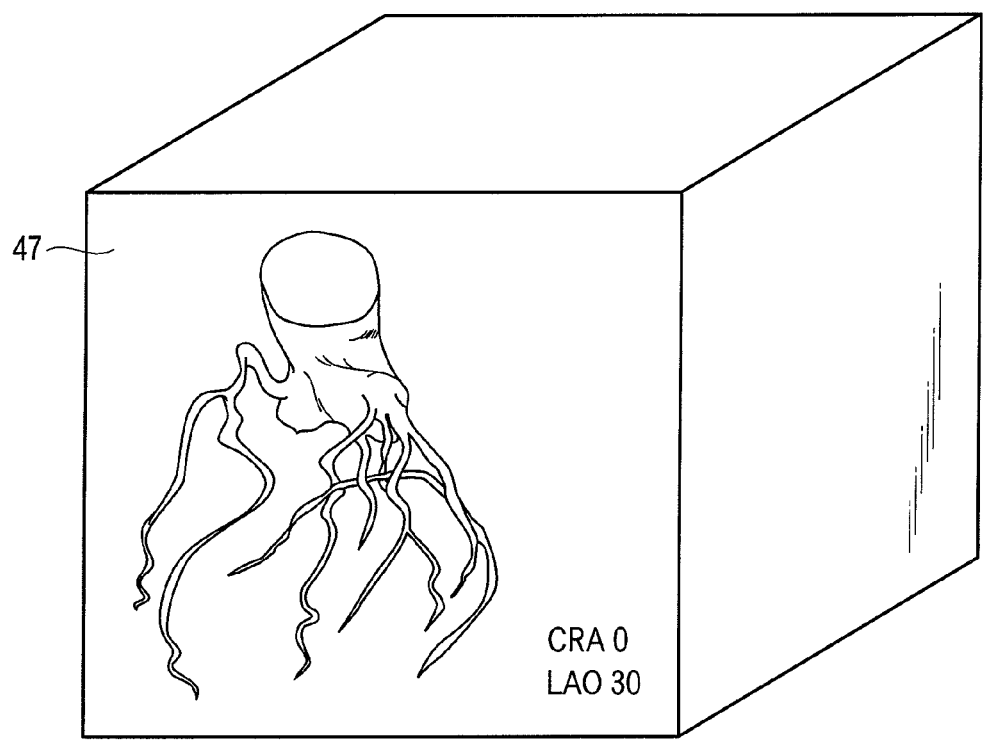
F I G. 11
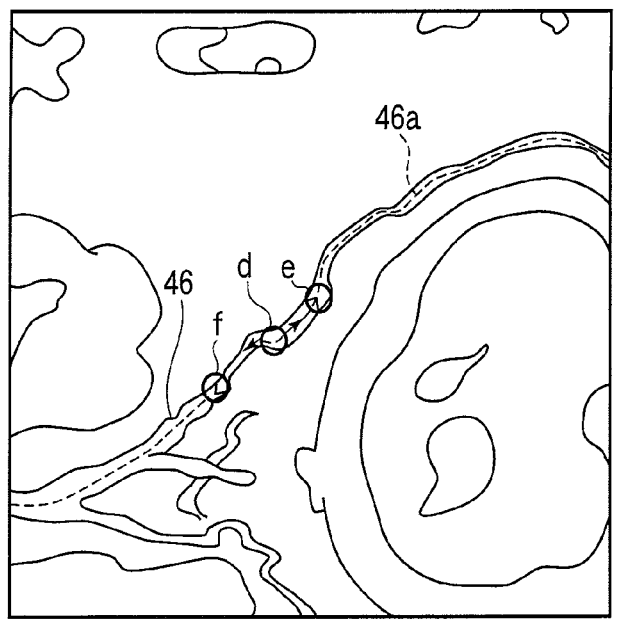
F I G. 13

Stretched CPR  →  Correspondence  Transformation to three-dimensional coordinate points  →

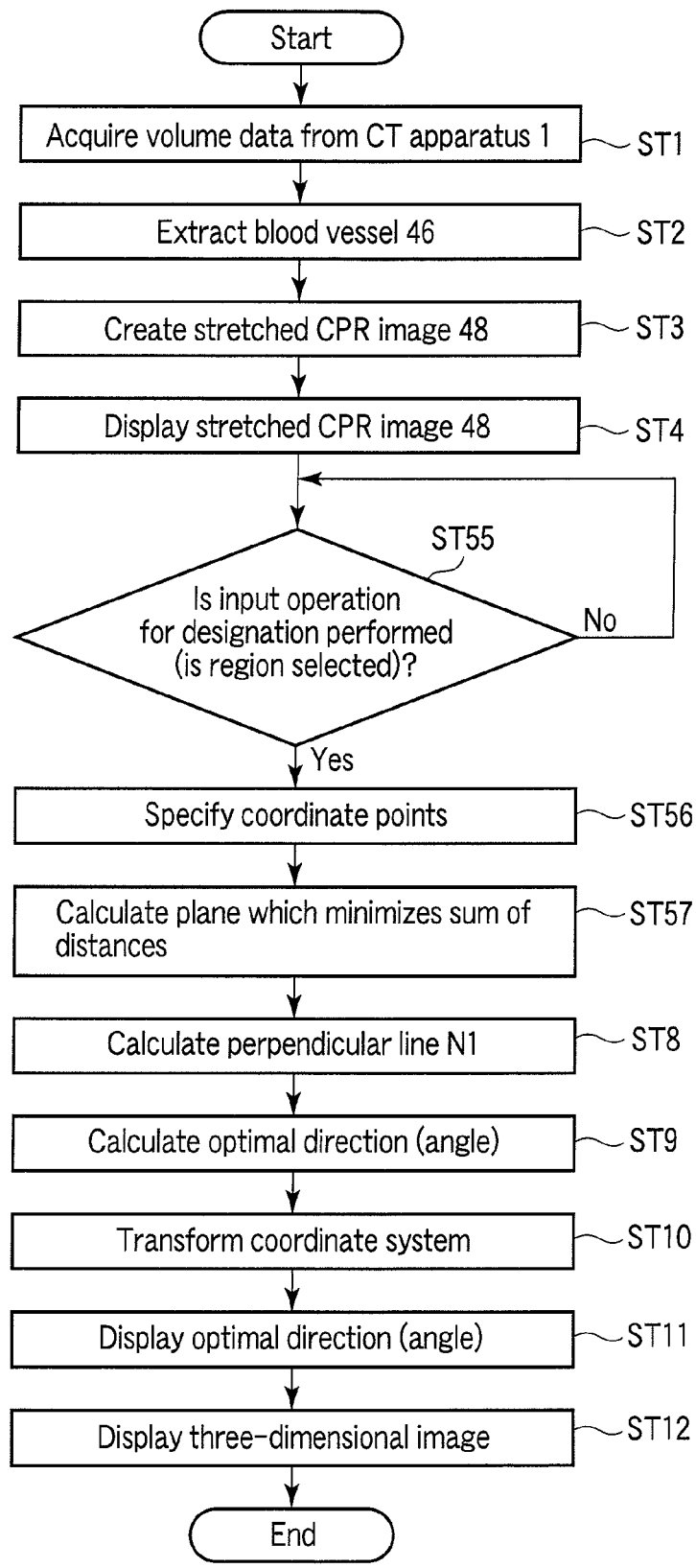
F I G. 19

Stretched CPR    Transformation to three-dimensional coordinate points

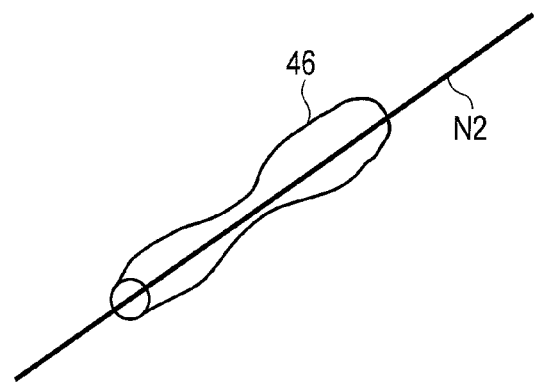
F I G. 27
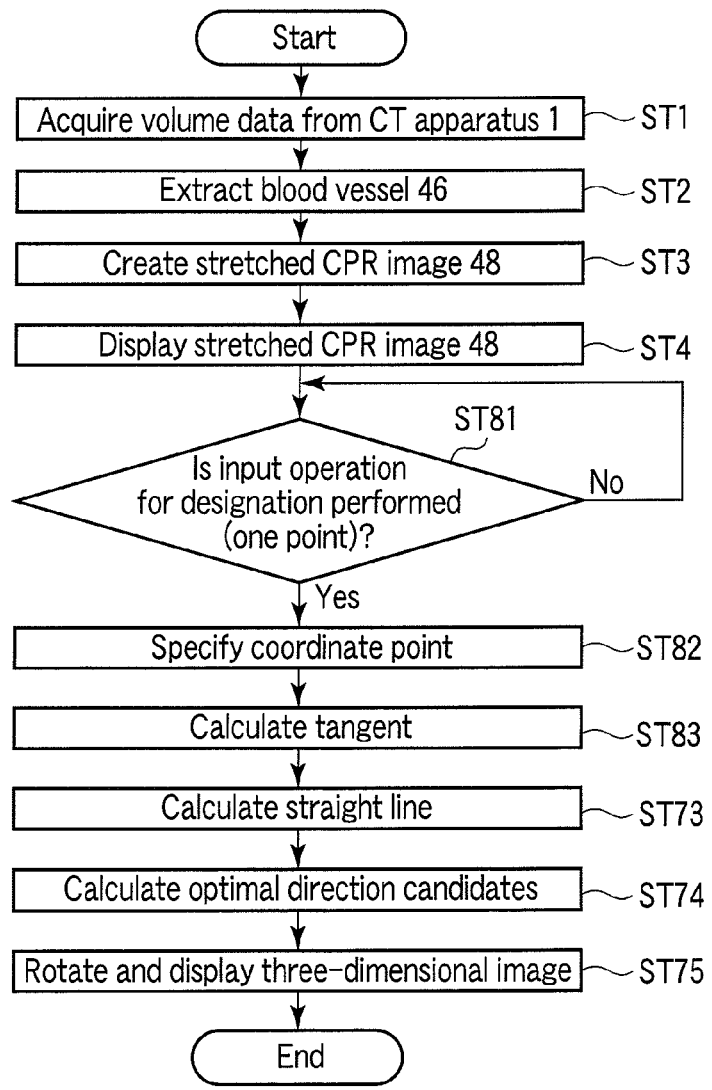
F I G. 28

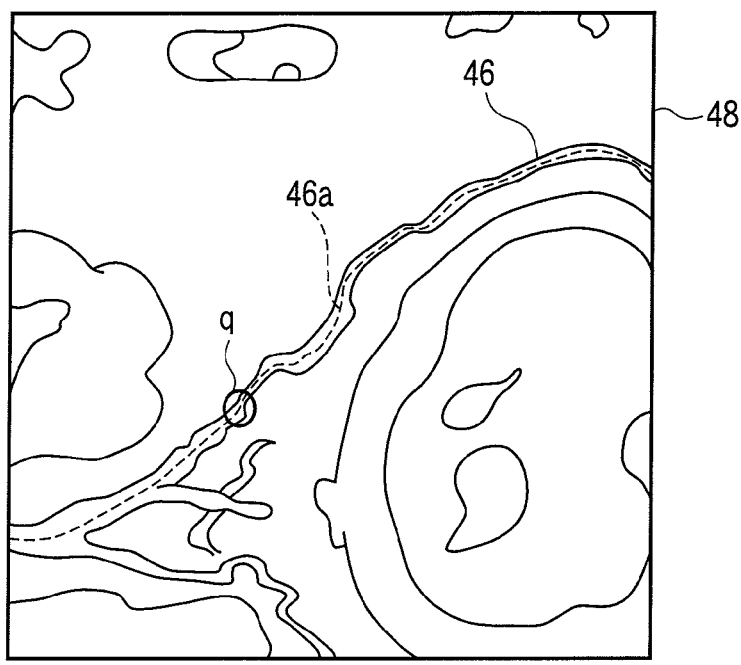
F I G. 29
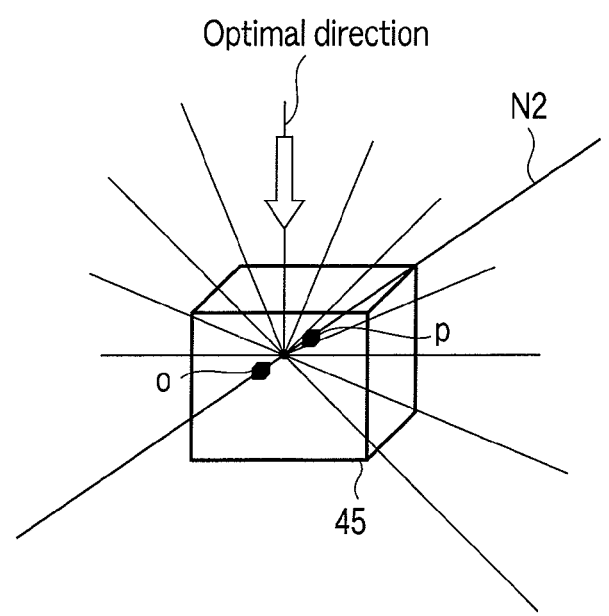
F I G. 31

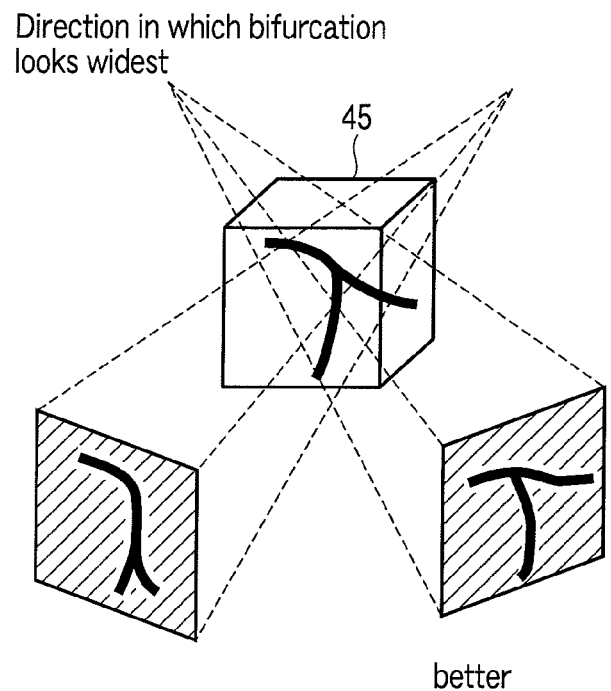
F I G. 40
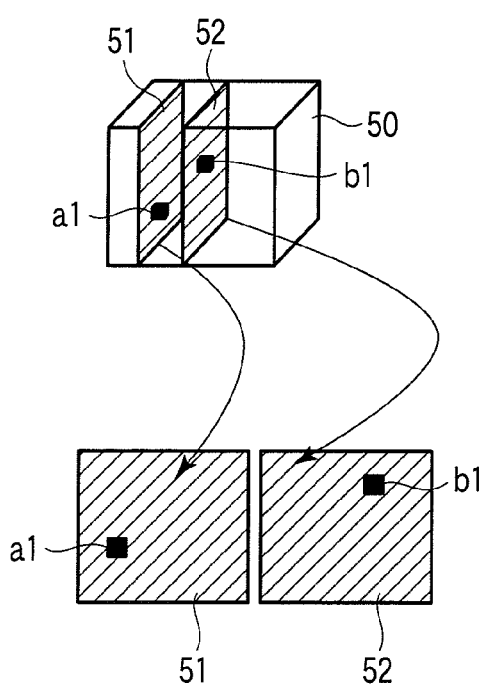
F I G. 41

DATA PROCESSING APPARATUS, X-RAY APPARATUS, AND DATA PROCESSING METHOD

CROSS-REFERENCE TO RELATED APPLICATIONS

This application is based upon and claims the benefit of priority from prior Japanese Patent Application No. 2008-033360, filed Feb. 14, 2008, the entire contents of which are incorporated herein by reference.

BACKGROUND OF THE INVENTION

1. Field of the Invention

The present invention relates to a data processing apparatus, an X-ray apparatus, and a data processing method.

2. Description of the Related Art

A medical image diagnostic technique using an X-ray diagnostic apparatus, an MRI apparatus, an X-ray CT apparatus, or the like has rapidly progressed with advances in computer technology of the 1970s. This technique has become indispensable to today's medical care.

X-ray diagnosis has recently improved mainly in the field of cardiovascular with advances in catheter techniques. X-ray diagnosis in a cardiovascular region is aimed at arteries and veins in the whole body. In many cases, X-ray transmission images are captured while a contrast agent is injected in blood vessels. An X-ray diagnostic apparatus for cardiovascular diagnosis generally includes an X-ray generating unit, an X-ray detecting unit, a holding mechanism which holds them, a bed (top), and a signal processing unit. As the holding mechanism, a C-arm or Ω-arm is used. Combining this arm with a top-cantilevered bed makes it possible to perform X-ray imaging from an optimal position or angle for a patient (to be referred to as the subject hereinafter).

As a detector used for the X-ray detecting unit of an X-ray diagnostic apparatus, an X-ray film or an image intensifier has been used. In an X-ray imaging method using this image intensifier, X-ray image information obtained when X-rays generated by the X-ray tube of the X-ray generating unit are applied to the subject and transmitted through the subject is converted into an optical image by the image intensifier. This optical image is captured by an X-ray TV camera and converted into an electrical signal. The X-ray image information converted into the electrical signal is digitized. The resultant image is displayed on a monitor. Therefore, the imaging method using the image intensifier allows real-time imaging which is impossible in the film system, and can acquire image data in the form of digital signals. This makes it possible to perform various kinds of image processing. As a substitute for the above image intensifier, a two-dimensional array X-ray flat panel detector (to be referred to as a flat panel detector hereinafter) has recently attracted attention. Some of such detectors have already been put into practical use.

In a conventional X-ray diagnostic apparatus having a C-arm, an imaging system is operated to set a desired imaging direction by moving the handle provided on a console. For example, in setting a C-arm tilt angle (working-angle) for coronary artery imaging, the following are required: (1) to image a blood vessel to be diagnosed without overlap of another blood vessel thereon; (2) to perpendicularly apply X-rays to the running direction of a blood vessel having a lesion region such as a stenosis region; and (3) to apply X-rays in a direction in which a bent portion can be easily observed. In order to meet such requirements, a doctor or a technician (to be referred to as an operator hereinafter) repeatedly performs X-ray imaging of the subject in a trial and error manner while changing the C-arm tilt angle, and observes the obtained fluoroscopic image data on the monitor, thereby setting an optimal X-ray imaging direction.

As disclosed in, for example, the specification of U.S. Pat. No. 6,424,731 (pages 1 to 4 and FIGS. 1 and 2), there is proposed a method of acquiring the three-dimensional image data of the subject in advance and setting an X-ray imaging direction on the basis of the obtained three-dimensional image data. In this method, the operator sets an optimal imaging direction by observing a three-dimensional image of the subject displayed on the display unit of the apparatus while rotating the image in a predetermined direction. The operator then sets a C-arm tilt angle on the basis of the set optimal imaging direction and performs X-ray imaging. As disclosed in, for example, Jpn. Pat. Appln. KOKAI Publication No. 2004-329729, there is provided a technique in which as a standard organ model is rotated, the arm of an X-ray apparatus rotates in accordance with the rotation of the model, thereby adjusting the angle of the arm. In addition, as disclosed in, for example, Jpn. Pat. Appln. KOKAI Publication No. 2007-20891, there is provided a technique of indicating the optimal arc of the pivotal movement of an X-ray apparatus in accordance with a point on a model which is designated by clicking.

Assume that when setting an optimal imaging direction for a morbid region such as a blood vessel, an operator who does not have sufficient anatomical knowledge or experience sets a C-arm tilt angle in a trial and error manner. In this case, since X-rays are applied to the subject many times, it takes much time to set a final imaging direction, resulting in an increase in X-ray exposure dose. In addition, since it is necessary to acquire three-dimensional image data of the subject in advance, the problems concerning the time required for overall X-ray imaging and the X-ray exposure dose of the subject have not still solved. Furthermore, in the above technique, it takes much time to determine, for example, an optimal direction so as to obtain images from many directions. In addition, it is difficult to apply this technique to actual patients with individual differences because of the use of a model. The problem of foreshortening cannot be solved because of the use of projected data.

The present invention has been made in consideration of such a situation, and has as its object to provide an X-ray diagnostic apparatus and X-ray imaging method which can shorten the time required for X-ray imaging and reduce the X-ray exposure dose of the subject by setting an optimal imaging direction using image data obtained in advance.

BRIEF SUMMARY OF THE INVENTION

An example of the present invention is a data processing apparatus comprising, a saving part configured to save three-dimensional data of a subject, a two-dimensional image display part configured to display three-dimensional data of the subject as a two-dimensional image, a designation part configured to designate coordinate information associated with a specific coordinate point on the two-dimensional image, a specifying part configured to specify, based on the coordinate information designated on the two-dimensional image, coordinate information on the corresponding three-dimensional data, and a calculation part configured to calculate a view angle of the subject on the basis of the coordinate information on the three-dimensional data.

An another example of the present invention is an X-ray apparatus comprising, the data processing apparatus, a X-ray generating part configured to apply X-rays to the subject, a X-ray detection part configured to detect X-rays applied from the X-ray generating part, a moving part configured to move the X-ray generating part and the X-ray detection part, and a movement control part configured to control movement of the moving part on the basis of the calculated view angle.

An another example of the present invention is an data processing method comprising steps of, displaying three-dimensional data of a subject as a two-dimensional image, designating coordinate information associated with a specific coordinate point on the two-dimensional image, specifying, based on the coordinate information designated on the two-dimensional image, coordinate information on the corresponding three-dimensional data, and calculating a view angle of the subject on the basis of the coordinate information on the three-dimensional data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 11 is a front view showing a state in which a projection image is displayed on a monitor in the first embodiment;

FIG. 13 is a view showing a display part and its operation sequence in the second embodiment;

FIG. 19 is a flowchart for explaining the operation of an image display apparatus in the fifth embodiment of the present invention;

FIG. 27 is a view for explaining an operation sequence in the seventh embodiment;

FIG. 28 is a flowchart for explaining the operation of an image display apparatus in the eighth embodiment of the present invention;

FIG. 29 is a view showing a display part and its operation sequence in the eighth embodiment;

FIG. 31 is a view for explaining an operation sequence in the ninth embodiment;

FIG. 40 is a view for explaining an operation sequence in the 12th embodiment; and FIG. 41 is a view for explaining the correspondence between a two-dimensional image and three-dimensional data in another embodiment of the present invention.

DETAILED DESCRIPTION OF THE INVENTION

[First Embodiment]

Figure 1:
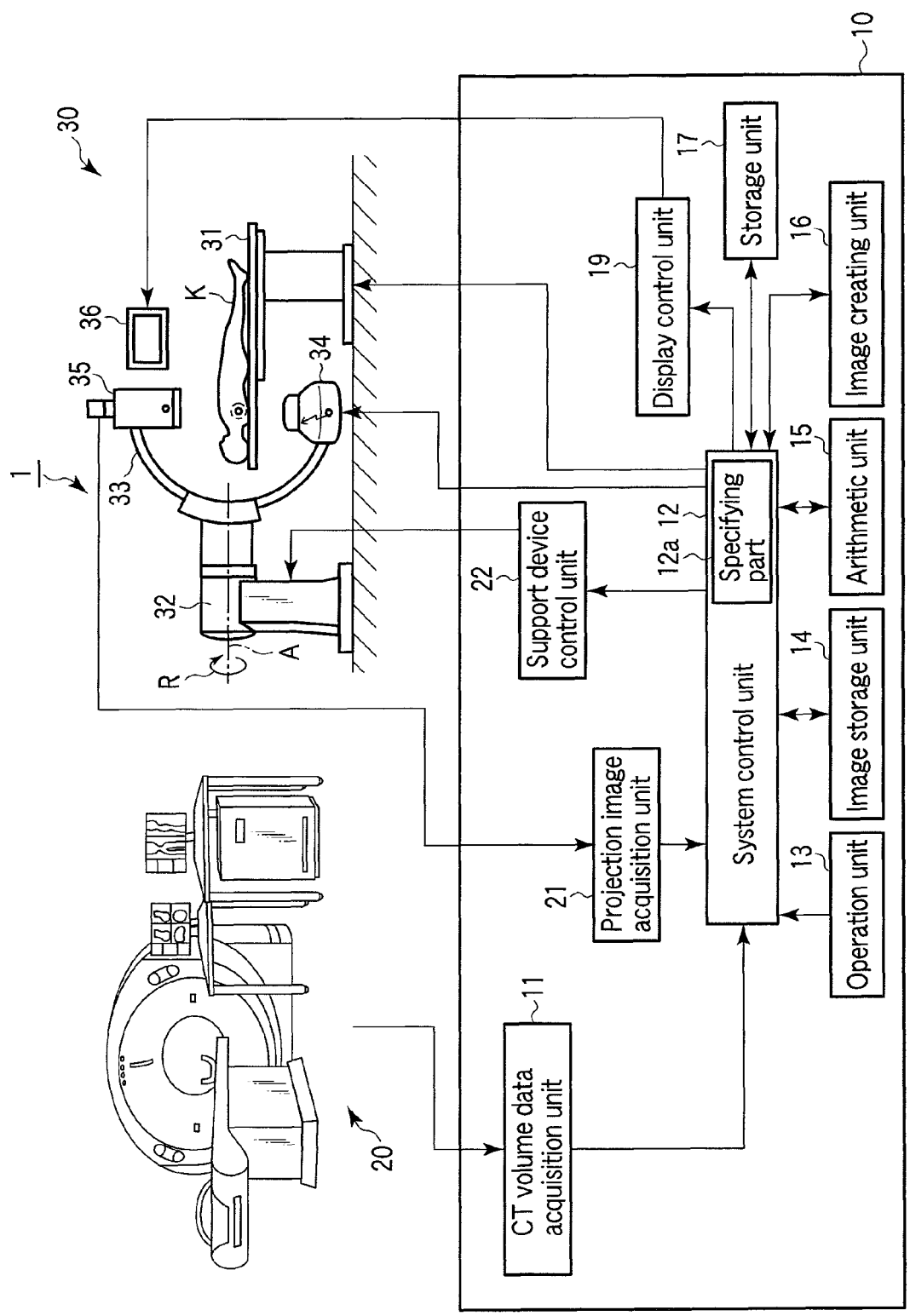
FIG. 1 is a block diagram showing the arrangement of an X-ray imaging system according to the first embodiment of the present invention.

A data processing apparatus, X-ray apparatus, and data processing method according to the first embodiment of the present invention will be described below with reference to the views of the accompanying drawing. FIG. 1 is a block diagram showing the arrangement of an X-ray system 1 according to the first embodiment of the present invention. The X-ray system 1 (X-ray apparatus) includes an image processing apparatus 10, a CT apparatus 20, and an X-ray imaging apparatus 30.

The image display apparatus (data processing apparatus) 10 shown in FIG. 1 includes a CT volume data acquisition unit 11, a system control unit 12, an operation unit 13 (designation part), an image storage unit 14 (saving part), an arithmetic unit 15 (calculation part), an image creating unit 16, a storage unit 17, a display control unit 19, a support device control unit 22, and a projection image acquisition unit 21. Note that the image processing apparatus 10 and the X-ray imaging apparatus 30 controlled by it constitute the X-ray system 1.

The CT volume data acquisition unit 11 serves to acquire CT volume data as desired three-dimensional data from the CT apparatus 20. The system control unit 12 controls the overall operation of the X-ray system 1. The operation unit 13 serves to perform operation for clicking a specific portion on a window, selection of an image, and the like, and includes a control panel. The system control unit 12 has a specifying part 12a configured to specify, based on the coordinate information designated on the two-dimensional image, coordinate information on the corresponding three-dimensional data.

The image storage unit 14 is a storage part configured to store three-dimensional volume data 45 and X-ray images. The arithmetic unit 15 serves to perform various arithmetic operations such as calculating an optimal direction on the basis of a specific position. The image creating unit 16 has a function of forming an image to be displayed on a monitor 36 (to be described later) in cooperation with the image storage unit 14. The storage unit 17 serves to store various kinds of information such as the information of the X-ray projecting direction of the X-ray imaging apparatus 30 (to be described later).

The display control unit 19 displays, on the monitor 36, various kinds of images such as cross sectional images of three-dimensional images and two-dimensional images created by the image storage unit 14 and the image creating unit 16. The support device control unit 22 controls the position and angle of a C-arm 33 of the X-ray imaging apparatus 30 (to be described later). The projection image acquisition unit 21 is a means for acquiring projection image data from an X-ray detector 35 (to be described later).

The X-ray imaging apparatus 30 includes a bed 31 on which a patient (subject) K is placed, a gantry 32, the C-arm 33 which is supported on the gantry 32 so as to be pivotal about the A-axis in FIG. 1 in the direction indicated by an arrow R in FIG. 1, an X-ray source 34 provided on one end portion of the C-arm 33, the X-ray detector 35 provided on the other end portion of the C-arm 33, and the monitor 36 (two-dimensional image display part or three-dimensional image display part) which displays a created image. The monitor 36 as a display part displays various kinds of images and information such as three-dimensional volume data and a two-dimensional CPR (Curved MPR) image.

The bed 31 can move in the vertical and horizontal directions. This makes it possible to properly place the patient K between the X-ray source 34 and the X-ray detector 35.

The C-arm 33 is structured to hold the X-ray source 34 and the X-ray detector 35 while making them face each other. Although not shown, the X-ray source 34 has an X-ray tube which applies X-rays to the patient K and a collimator which collimates the X-rays applied from the X-ray tube. The X-ray detector 35 includes, for example, an image intensifier and an optical system. The image intensifier converts X-ray information transmitted through the patient K into optical information. The optical system focuses this optical information by using an optical lens. Note that an X-ray flat panel detector can be used as a detection device other than the image intensifier.

The monitor 36 displays, on a window, various kinds of information such as volume images and two-dimensional images output via the display control unit 19.

A control sequence in the system control unit 12 of the image display apparatus and the operation of each apparatus in the first embodiment of the present invention will be described next with reference to the flowchart of FIG. 2.

In this case, as a two-dimensional image, a stretched CPR (Curved Planar Reconstruction) image by CT is used. This stretched CPR image by CT is characterized in that a blood vessel is extracted without foreshortening, and the pixel positions of a two-dimensional image which is being displayed correspond one-to-one with those of the volume data of a three-dimensional image. That is, a CPR image is a two-dimensional image indicating an arbitrary section of the volume data of a three-dimensional image, and each pixel of the CPR image is made to correspond to a corresponding one of the voxels of the volume data of a three-dimensional image. Inversely using the transformation formula used to create a CPR image as an arbitrary section from the volume data of a three-dimensional image makes it possible to obtain a voxel of volume data which corresponds to a pixel on the CPR image.

When pixel coordinate points on a stretched CPR image by CT which is expressed two-dimensionally are clicked, since the pixels of the image correspond one-to-one with voxels, three-dimensional coordinate points can be obtained. Obtaining the three three-dimensional coordinate points can define a plane in a space. A direction perpendicular to this plane is output as an optimal view angle (working angle). Note that in this case, a pixel indicates each pixel in a two-dimensional coordinate system, and voxel indicates each data in a three-dimensional image.

Figure 2:
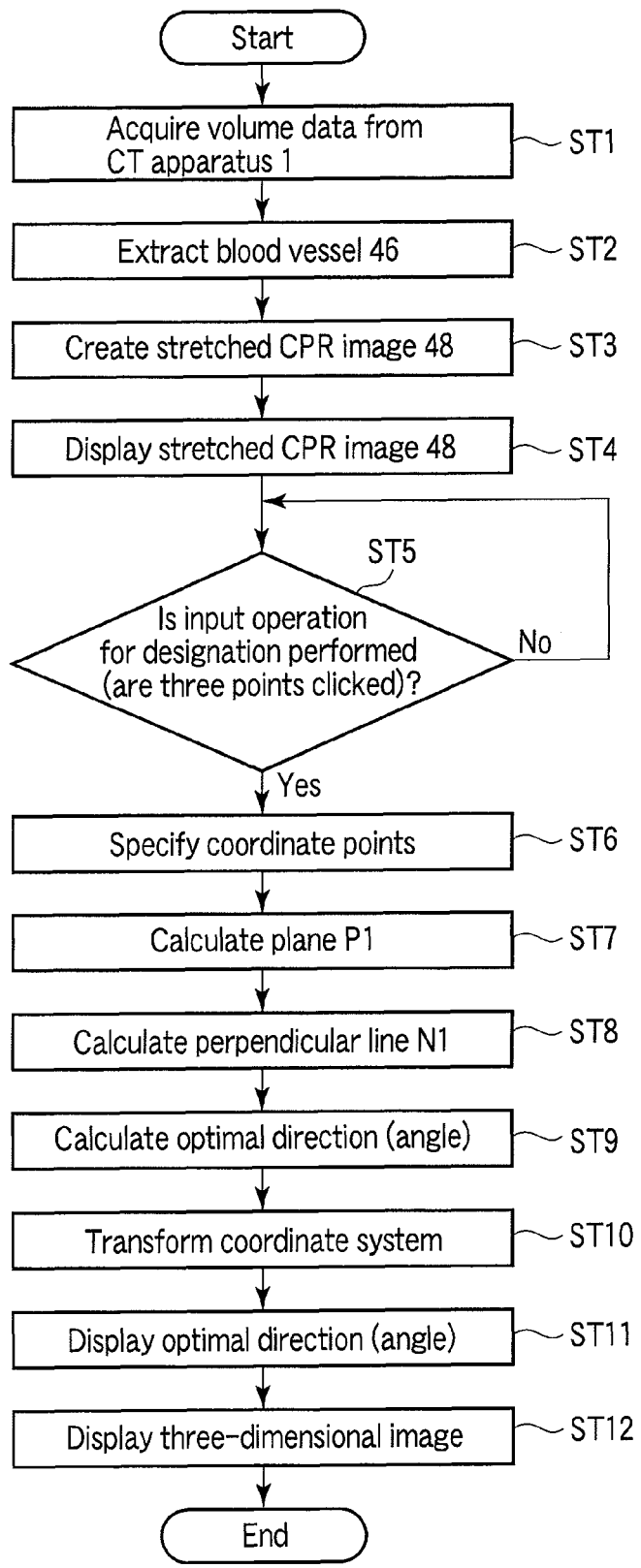
FIG. 2 is a flowchart for explaining the operation of an image display apparatus according to the first embodiment.

As shown in FIG. 2, first of all, a stretched CPR image of a target blood vessel is created from the CT volume data acquired by the CT volume data acquisition unit 11 upon imaging and reconstruction by the CT apparatus 20 before surgery.

Figure 3:
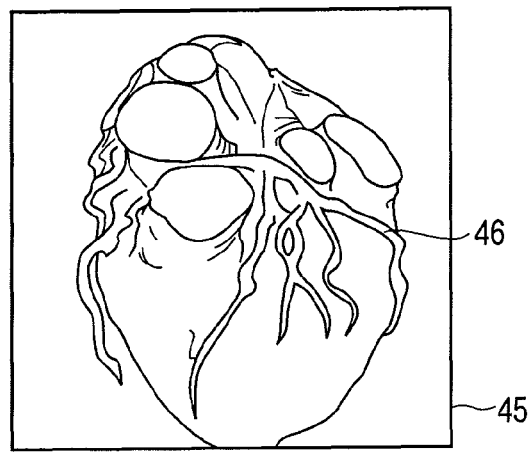
FIG. 3 is a view for explaining volume data in the first embodiment.
Figure 4:
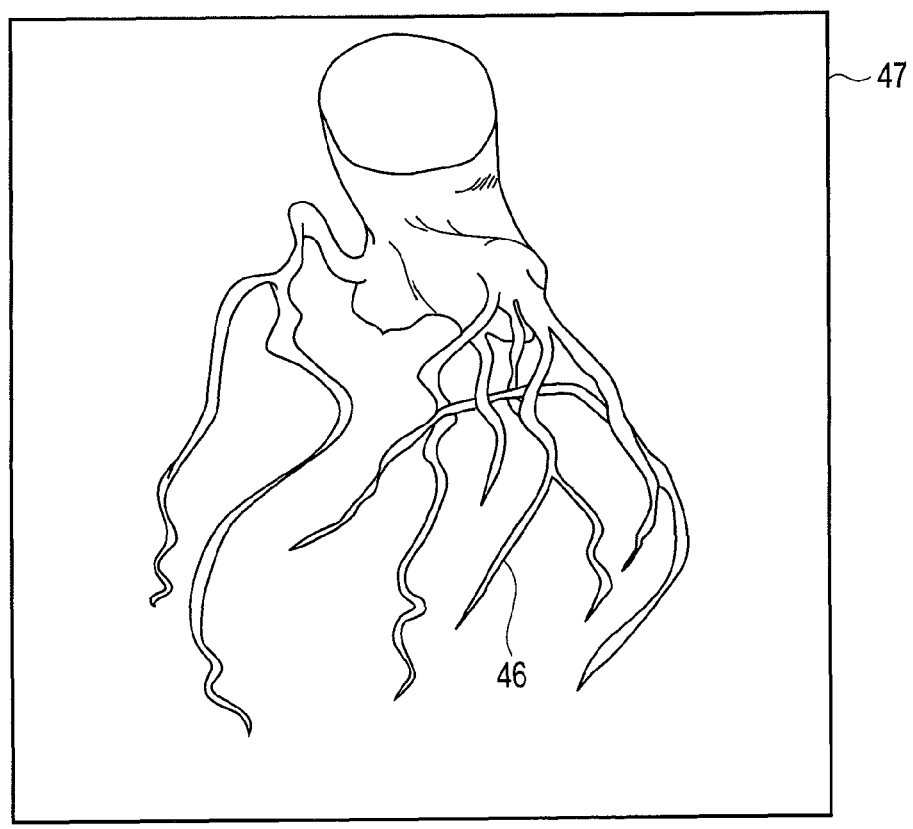
FIG. 4 is a view for explaining an extracted image in the first embodiment.

More specifically, in step ST1, the volume data 45 shown in FIG. 3 is obtained from the CT apparatus 20 shown in FIG. 1. A blood vessel 46 portion is extracted from the volume data 45 (ST2). FIG. 4 shows an extracted blood vessel extraction image 47.

Note that this technique is often used for a stenosis, aneurysm, total occlusion, or bifurcated region. The shape of such a blood vessel may be bifurcated or disconnected. Such cases will be described later in other embodiments. The following exemplifies a case in which a blood vessel has a predetermined shape which continuously extends as shown in FIG. 5.

Figure 5:
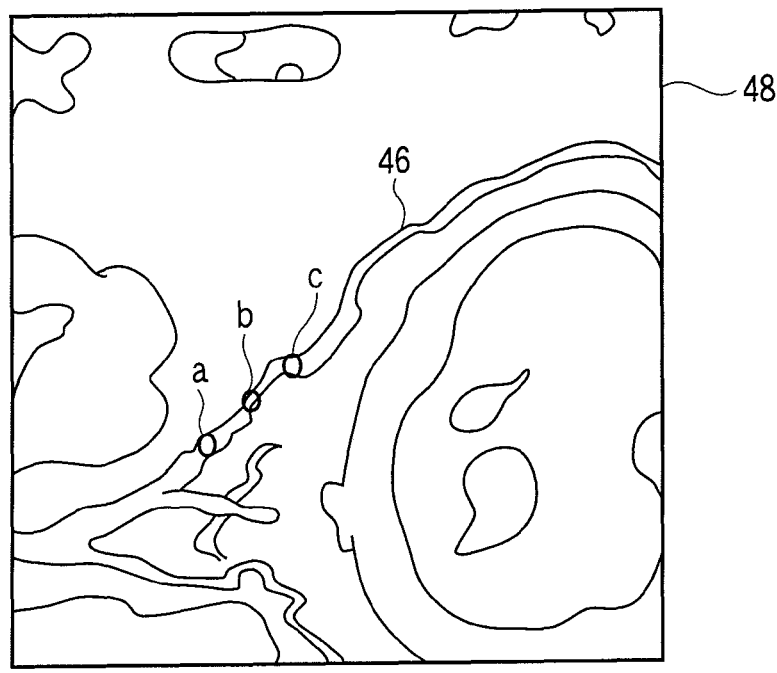
FIG. 5 is a view for explaining a two-dimensional image in the first embodiment.

Subsequently, a stretched CPR image 48 of the target blood vessel 46 like that shown in FIG. 5 is created (ST3). This image is the stretched CPR image 48 of a two-dimensional blood vessel. The stretched CPR image 48 of the blood vessel 46 is a sectional view taken along a blood vessel of the volume data 45. The stretched CPR image 48 of this blood vessel is displayed on the monitor 36 (ST4).

Figure 6:
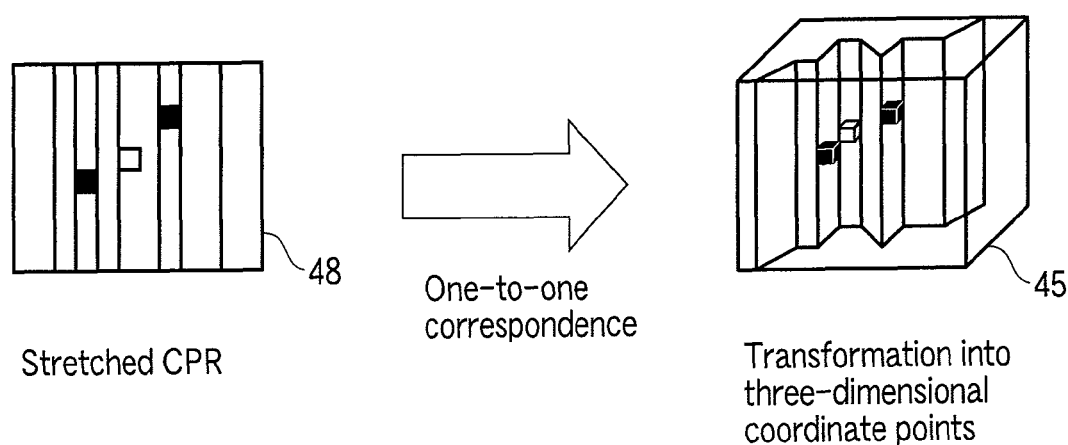
FIG. 6 is a view for explaining the correspondence between a two-dimensional image and volume data in the first embodiment.

There are three types of CPR images. In this case, a stretched CPR image is used. However, it suffices to use a straightened CPR image. Both types of images are characterized in that the length of a blood vessel is kept the same, and pixels correspond one-to-one with three-dimensional coordinate points, as shown in FIG. 6.

Subsequently, the operator designates a designation point on a vascular stretched CPR image displayed on the monitor 36 by operating the operation unit 13, e.g., clicking the operation unit 13 (ST5). As shown in FIG. 5, for example, the operator designates three points a, b, and c on the vascular stretched CPR image 48 by clicking three portions near a morbid region (e.g., a stenosis) which is a portion which the operator wants to see on the CPR image. This clicking operation is performed with a mouse or keyboard included in the operation unit 13, a touch panel, or the like.

Assume that three points are specified on a two-dimensional image in this manner. In this case, as shown in FIG. 6, since one pixel corresponds to one voxel of volume data, the arithmetic unit 15 transforms the three points on the stretched CPR image into three-dimensional coordinate points by, for example, inversely using the transformation formula used to obtain the stretched CPR image from the three-dimensional data, thereby specifying three three-dimensional coordinate points (ST6).

Figure 7:
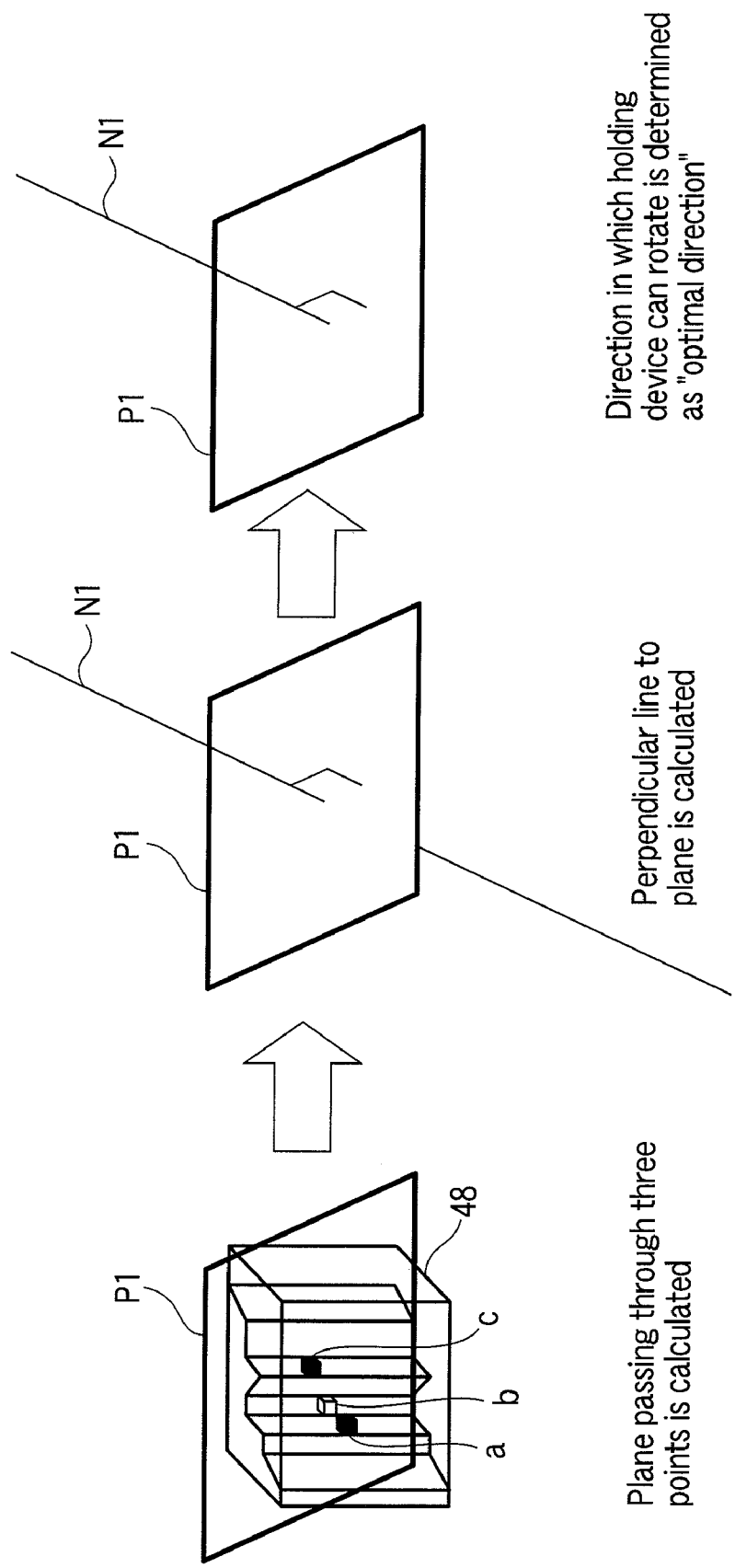
FIG. 7 is a view for explaining an operation sequence in the first embodiment.
Figure 8:
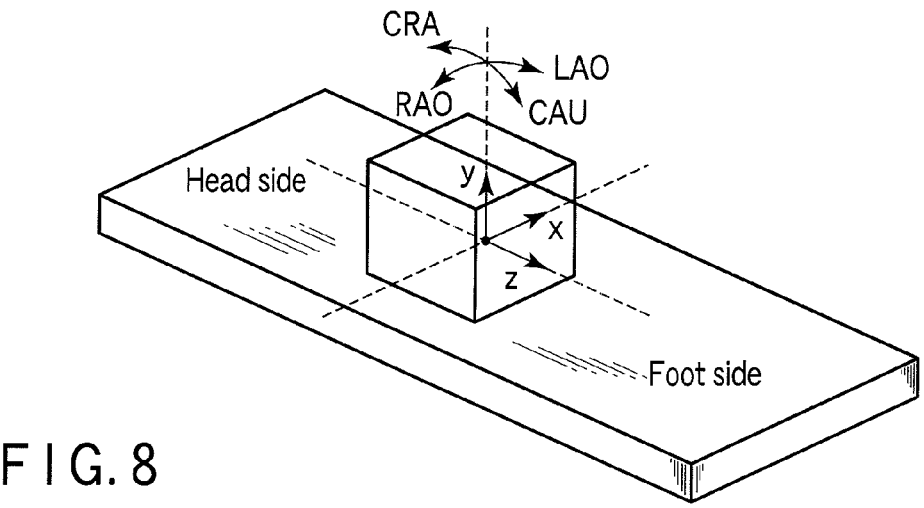
FIG. 8 is a view for explaining a coordinate system transformation method in the first embodiment.
Figure 9:
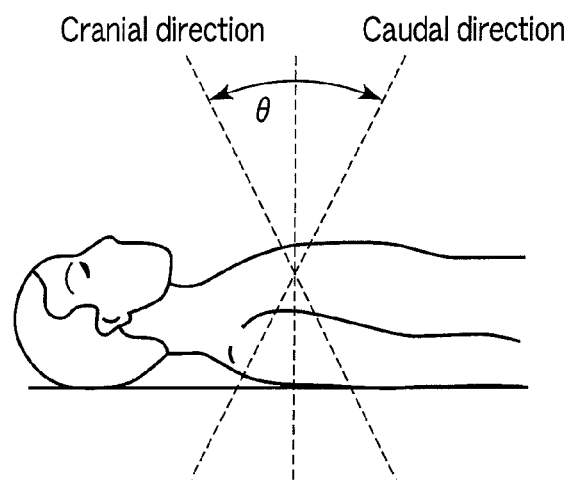
FIG. 9 is a view for explaining the coordinate system transformation method in the first embodiment.
Figure 10:
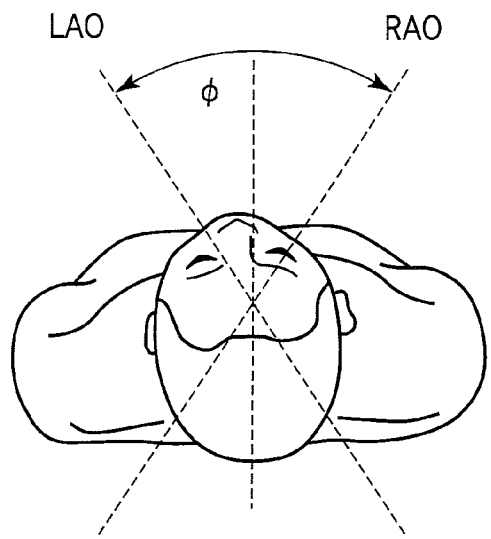
FIG. 10 is a view for explaining the coordinate system transformation method in the first embodiment.

As shown in FIG. 7, since the three points on the vascular stretched CPR image 48 respectively serve as three-dimensional coordinate points, a plane in a dimensional space which passes through the three points can be uniquely determined. The arithmetic unit 15 calculates a mathematical expression representing a plane P1 passing through the three points on the basis of the obtained three three-dimensional coordinate points (ST7).

The arithmetic unit 15 then calculates a perpendicular line N1 to the plane P1 (ST8). The direction of the perpendicular line N1 is the direction in which the three points look most spaced apart from each other. Two directions 180° apart from each other are calculated as the directions of the perpendicular line N1. One of these directions is the direction in which the X-ray imaging apparatus 30 cannot rotate depending on the mechanical restrictions imposed on the X-ray imaging apparatus 30. The arithmetic unit 15 calculates, as an optimal view angle, an angle which satisfies a condition for the direction of the perpendicular line N1 and a condition that the apparatus can pivot within the range of the angle, on the basis of information associated with the X-ray imaging apparatus 30, e.g., the range in which the C-arm 33 of the X-ray imaging apparatus 30 can pivot (ST9).

The coordinate system associated with the obtained optimal view angle is transformed (ST10). In general, a three-dimensional coordinate system like an X-Y-Z coordinate system is often used for volume data. A coordinate system commonly used in an X-ray system is often expressed by the LAO/RAO or CRA/CAU system with the center of the support device being 0. The relationship between them can be uniquely transformed by assuming that the center of the volume data and the center of the support device are 0. This makes it possible to express the obtained optimal view angle by the LAO/RAO or CRA/CAU system.

As shown in FIG. 11, the obtained optimal view angle is output as a number to the monitor 36 and displayed (ST11). For example, this information is displayed like "CRA: 0°, LAO: 30°". At the same time, the three-dimensional image displayed on the monitor is rotated in a direction corresponding to the optimal direction and displayed (ST12). That is, a rotated CT projection image is created by the image creating unit 16, and the CT projection image 46 of the blood vessel seen from the direction is displayed on the monitor 36.

Information associated with the determined optimal direction is sent to the support device control unit 22 (ST13). In addition, the information associated with the optimal direction is temporarily stored in the storage unit 17 (ST14).

The support device control unit 22 then controls the C-arm 33 to locate the apparatus in the optimal direction in accordance with the angle stored in the storage unit 17 (ST15).

The data processing apparatus, X-ray apparatus, and data processing method according to this embodiment have the following effects. Setting an optimal imaging direction for an imaging target region in advance by using a CT image or the like can shorten the time required for X-ray imaging and reduce the X-ray exposure dose of the subject. For example, the optimal direction of the X-ray apparatus can be calculated on the basis of an image obtained in advance by only clicking a morbid region (occlusion, stenosis, or bifurcation) on a blood vessel which the operator wants to see.

Using a CT image, in particular, makes it possible to create a three-dimensional image by extracting only a blood vessel. In addition, since even a blood vessel which a contrast agent is difficult to clearly enter, e.g., a totally occluded blood vessel, can be visualized by using a CT image, a more proper angle can be calculated.

In addition, CPR images are frequently used to observe a stenosis or determine an approximate stent length. This also makes it possible to obtain the effect of easily obtaining an optimal view angle suitable for an intervention treatment of a morbid region by designating a morbid region (occlusion, stenosis, or bifurcation) which the operator wants to see on this CPR image.

[Second Embodiment]

A data processing apparatus, X-ray apparatus, and data processing method according to the second embodiment of the present invention will be described next with reference to FIGS. 12 and 13. Note that the data processing apparatus, X-ray apparatus, and data processing method according to this embodiment are the same as those according to the first embodiment except for steps ST25 to ST27, and hence description will not be repeated.

Figure 12:
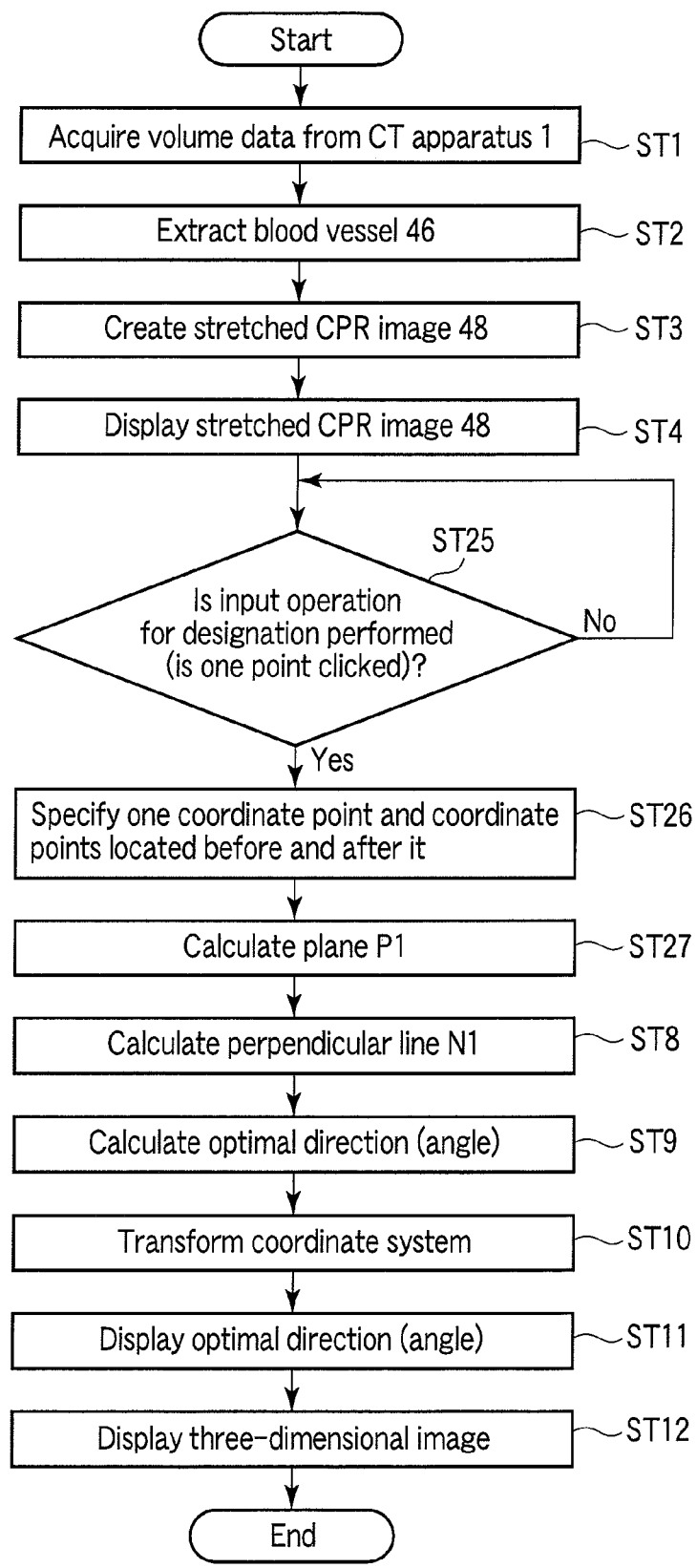
FIG. 12 is a flowchart for explaining the operation of an image display apparatus in the second embodiment of the present invention.

In this embodiment, as shown in FIG. 12, after the processing in steps ST1 to ST4 is performed as in the first embodiment, the operator designates one desired portion near a morbid region (stenosis) by clicking, thereby designating one point d, as shown in, for example, FIG. 13 (ST25).

Note that as volume data, volume data obtained upon extraction of a vascular center coordinate points is used. In an actual clinical setting, since the operator traces a vascular centerline 46a after CT imaging, it suffices to use the data of the vascular centerline 46a unchanged.

In this case, based on the already extracted vascular centerline 46a, the coordinate points e and f on the two sides of one designated point d, which are spaced apart by predetermined distances along the vascular centerline 46a, are respectively specified (ST26). The plane P1 passing through the two points e and f and the one point d is calculated (ST27). Other processes are the same as those in the first embodiment.

The data processing apparatus, X-ray apparatus, and data processing method according to this embodiment can obtain the same effects as those obtained by the data processing apparatus, X-ray apparatus, and data processing method according to the first embodiment.

[Third Embodiment]

A data processing apparatus, X-ray apparatus, and data processing method according to the third embodiment of the present invention will be described next with reference to FIGS. 14 and 15. Note that the data processing apparatus, X-ray apparatus, and data processing method according to this embodiment are the same as those according to the first and second embodiments except for steps ST35 to ST37, and hence description will not be repeated.

Figure 14:
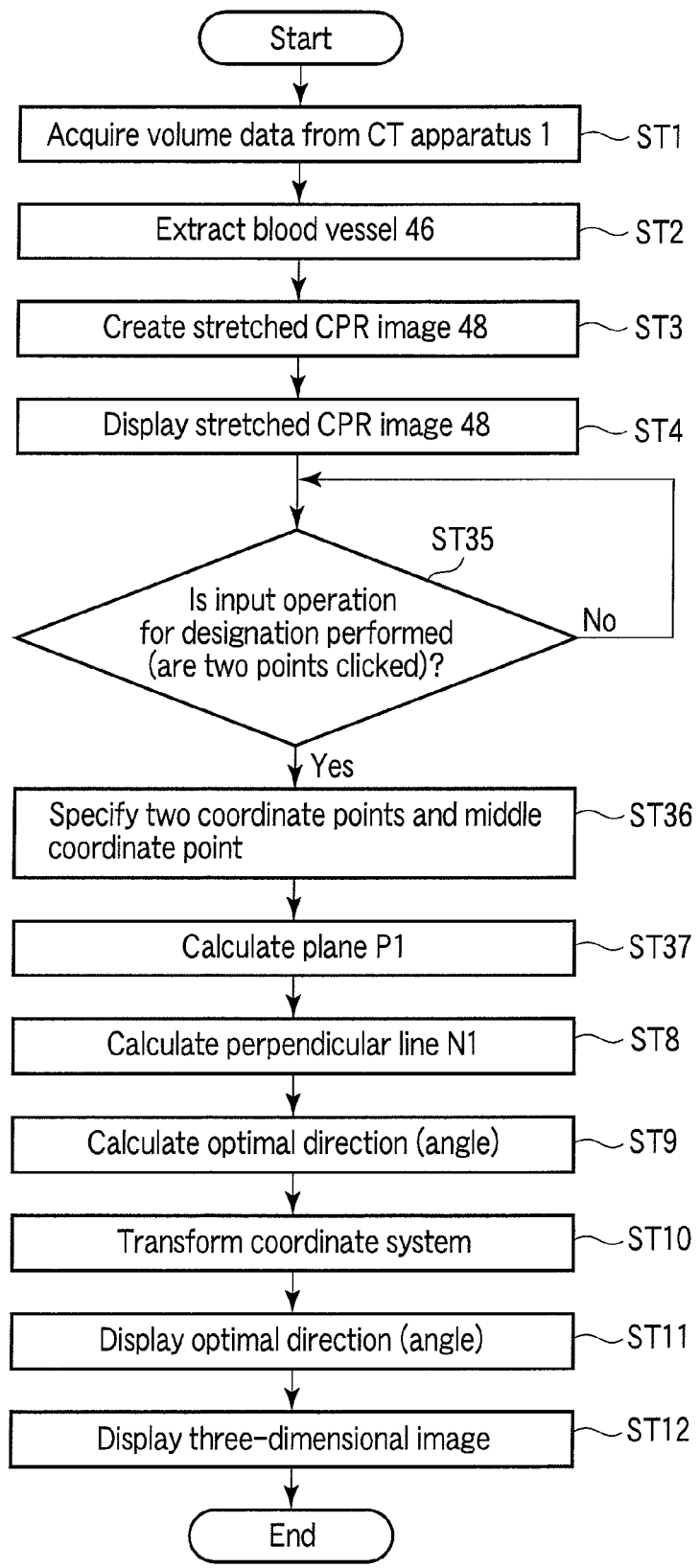
FIG. 14 is a flowchart for explaining the operation of an image display apparatus in the third embodiment of the present invention.
Figure 15:
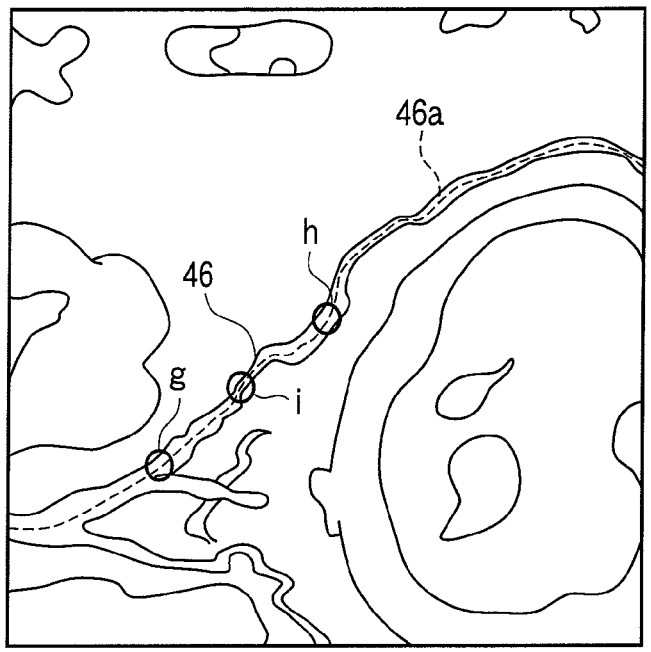
FIG. 15 is a view showing a display part and its operation sequence in the third embodiment.

In this embodiment, as shown in FIG. 14, after the processing in steps ST1 to ST4 is performed as in the first embodiment, the operator designates two desired portions near a morbid region (stenosis) by clicking, thereby designating two points g and h (ST35), as shown in, for example, FIG. 15.

In this case, based on an already extracted vascular centerline 46*a*, the middle coordinate point i which is located between the two designated portions along the vascular centerline 46*a* are specified (ST36). A plane P1 passing through the one mid-point i and the two designated points g and h is calculated (ST37). Other processes are the same as those in the first and second embodiments.

The data processing apparatus, X-ray apparatus, and data processing method according to this embodiment can obtain the same effects as those obtained by the data processing apparatus, X-ray apparatus, and data processing method according to the first and second embodiments.

[Fourth Embodiment]

A data processing apparatus, X-ray apparatus, and data processing method according to the fourth embodiment of the present invention will be described next with reference to FIGS. 16 to 18. Note that the data processing apparatus, X-ray apparatus, and data processing method according to this embodiment are the same as those according to the first to third embodiments except for steps ST45 to ST47, and hence description will not be repeated.

Figure 17:
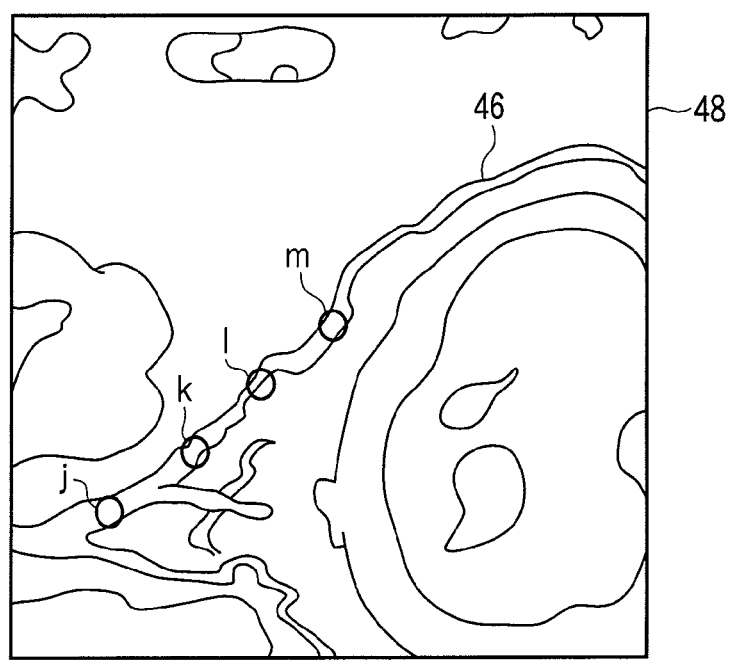
FIG. 17 is a view showing a display part and its operation sequence in the fourth embodiment.
Figure 16:
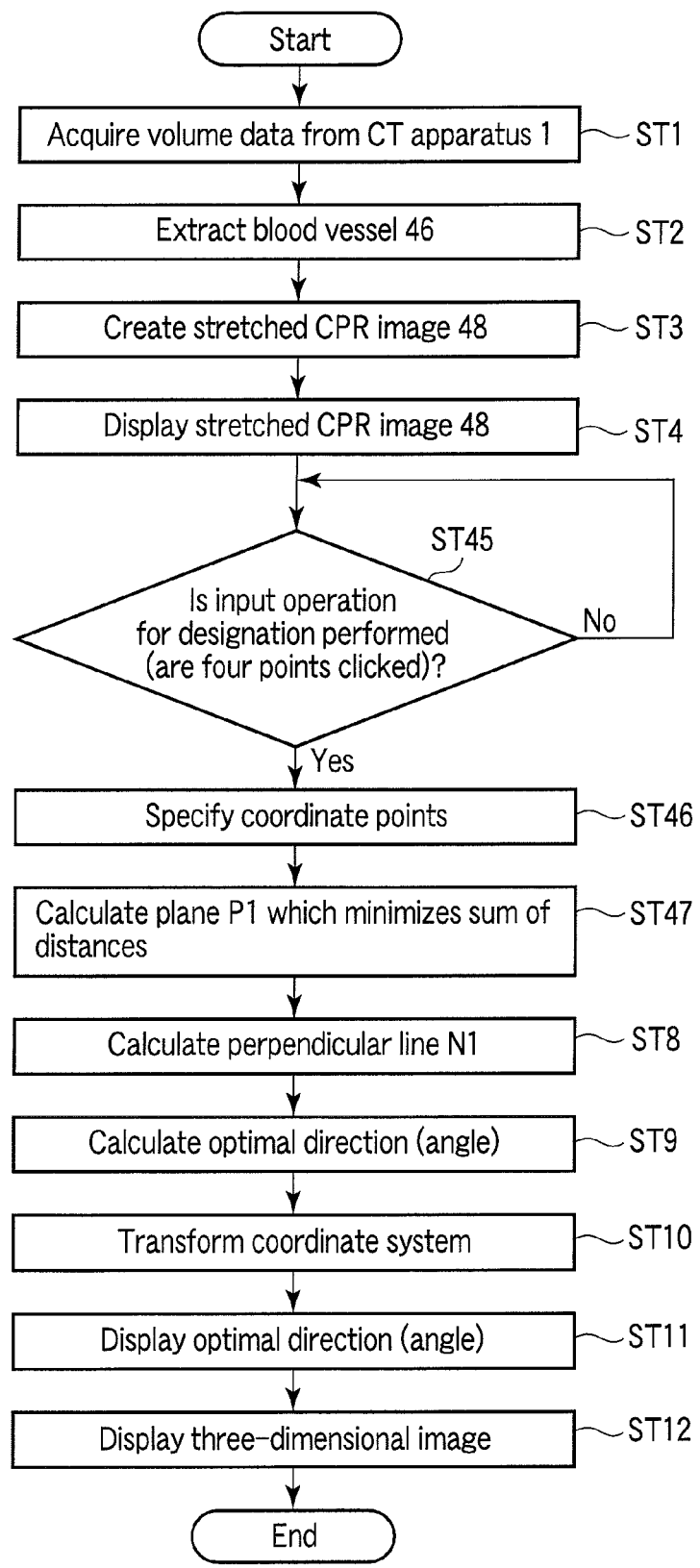
FIG. 16 is a flowchart for explaining the operation of an image display apparatus in the fourth embodiment of the present invention.

In this embodiment, as shown in FIG. 16, after the processing in steps ST1 to ST4 is performed as in the first embodiment, the operator designates four desired portions near a morbid region (stenosis) by clicking, thereby designating four points j, k, l, and m (ST45), as shown in, for example, FIG. 17. The four coordinate points j, k, l, and m are specified (ST46).

Figure 18:
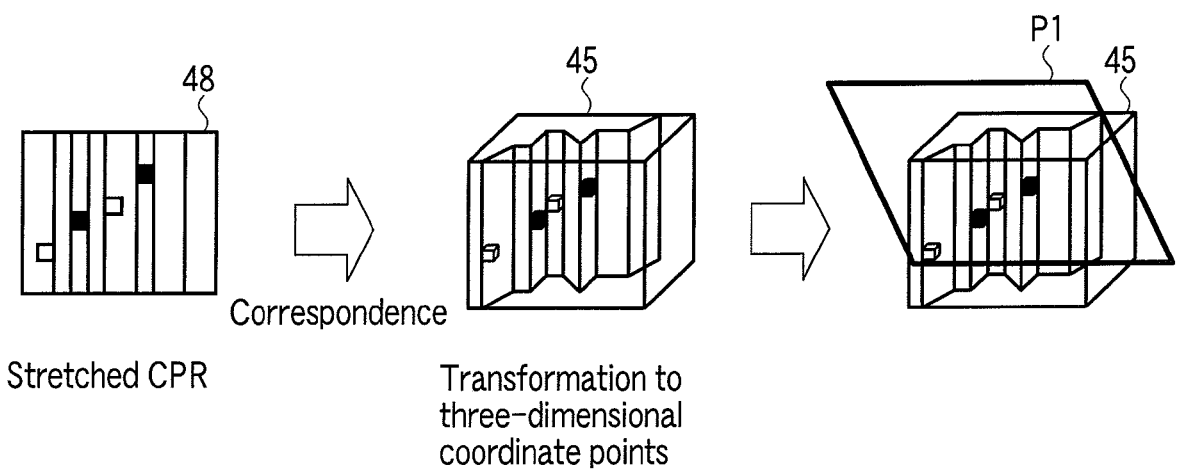
FIG. 18 is a view for explaining an operation sequence in the fourth embodiment.

In this case, since a plane is not uniquely determined, a plane which minimizes the sum of the distances from four points is sequentially calculated and estimated, and a plane which minimizes the sum of the distances is calculated and specified as a plane P1, as shown in FIG. 18 (ST47). Other processes are the same as those in the first to third embodiments.

The data processing apparatus, X-ray apparatus, and data processing method according to this embodiment can obtain the same effects as those obtained by the data processing apparatus, X-ray apparatus, and data processing method according to the first to third embodiments.

[Fifth Embodiment]

A data processing apparatus, X-ray apparatus, and data processing method according to the fifth embodiment of the present invention will be described next with reference to FIGS. 19 and 20. Note that the data processing apparatus, X-ray apparatus, and data processing method according to this embodiment are the same as those according to the first to fourth embodiments except for steps ST55 to ST57, and hence description will not be repeated.

Figure 20:
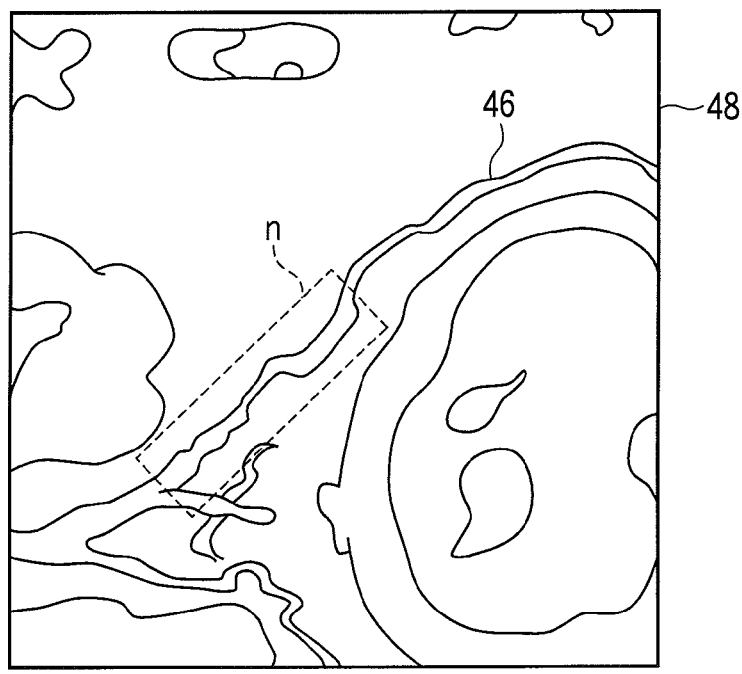
FIG. 20 is a view showing a display part and its operation sequence in the fifth embodiment.

In this embodiment, as shown in FIG. 19, after the processing in steps ST1 to ST4 is performed as in the first embodiment, the operator designates a desired region n near a morbid region (stenosis) by clicking, thereby designating many points in the region n (ST55), as shown in, for example, FIG. 20. The many coordinate points are specified (ST56).

In this case, since a plane is not uniquely determined, as in the fourth embodiment, a plane which minimizes the sum of the distances from the respective points is sequentially calculated and estimated, and a plane which minimizes the sum of the distances is calculated and specified as a plane P1, as shown in FIG. 18 (ST57). Other processes are the same as those in the first to fourth embodiments.

The data processing apparatus, X-ray apparatus, and data processing method according to this embodiment can obtain the same effects as those obtained by the data processing apparatus, X-ray apparatus, and data processing method according to the first to fourth embodiments.

[Sixth Embodiment]

A data processing apparatus, X-ray apparatus, and data processing method according to the sixth embodiment of the present invention will be described next with reference to FIG. 21. Note that the data processing apparatus, X-ray apparatus, and data processing method according to this embodiment are the same as those according to the first to fifth embodiments except for steps ST61 to ST63, and hence description will not be repeated.

Figure 21:
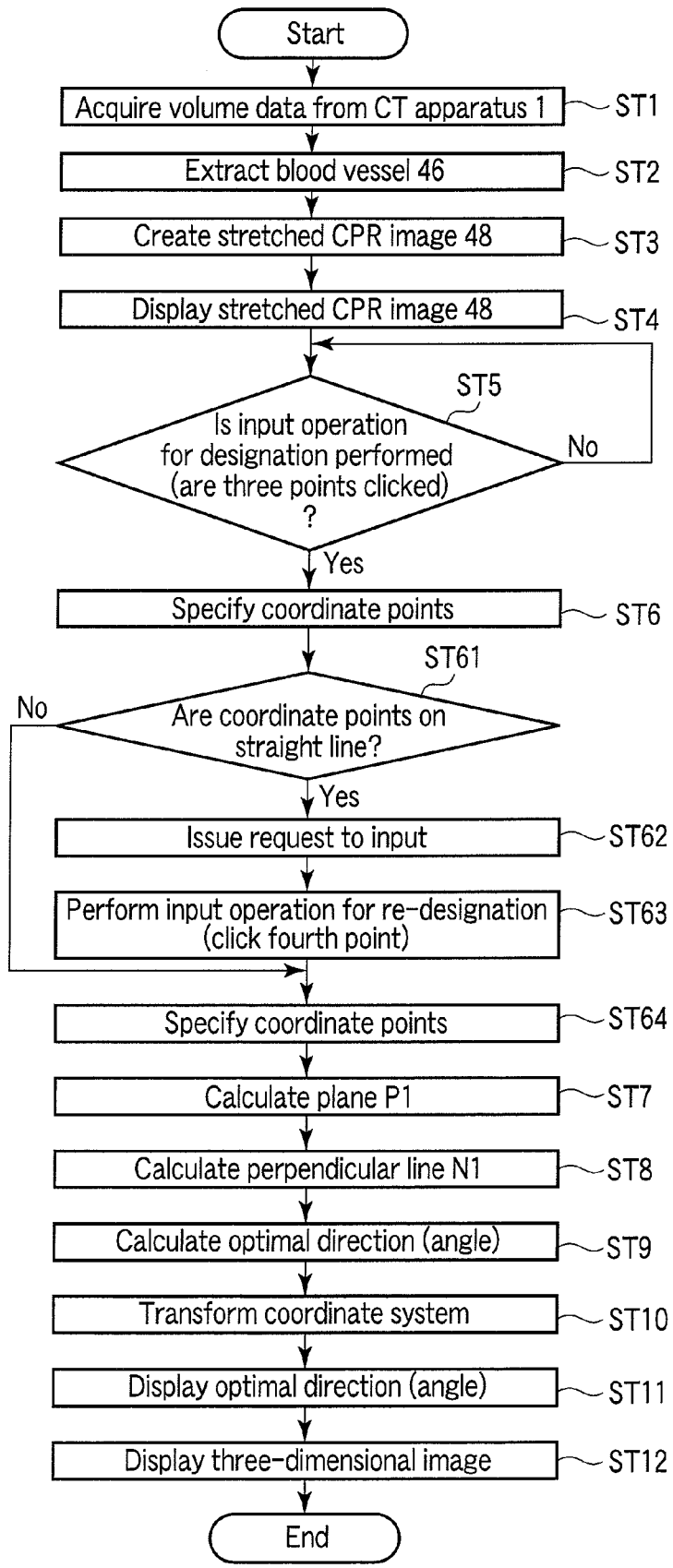
FIG. 21 is a flowchart for explaining the operation of an image display apparatus in the sixth embodiment of the present invention.

In this embodiment, as shown in FIG. 21, after the processing in steps ST1 to ST6 is performed as in the first embodiment, it is determined whether the three points designated by the operator are located on a straight line (ST61). If they are located on a straight line, since a plane is not uniquely determined, a request to perform further input operation is issued (ST62). For example, a message or the like is displayed on a display part to prompt the operator to designate another portion.

When the operator performs input operation for designation again in response to this input request (ST63), a plane P1 passing through the points including the added point is calculated (ST7). This re-designation is performed by, for example, further clicking one portion.

Other processes are the same as those in the first to fifth embodiments.

The data processing apparatus, X-ray apparatus, and data processing method according to this embodiment can obtain the same effects as those obtained by the data processing apparatus, X-ray apparatus, and data processing method according to the first to fifth embodiments.

As a modification of this embodiment, it suffices to automatically perform the processing in steps ST73 to ST75 in the seventh embodiment (to be described later) instead of issuing a request for designation when three points are located on a straight line.

[Seventh Embodiment]

A data processing apparatus, X-ray apparatus, and data processing method according to the seventh embodiment of the present invention will be described next with reference to FIGS. 22 to 27. Note that the data processing apparatus, X-ray apparatus, and data processing method according to this embodiment are the same as those according to the first to sixth embodiments except for steps ST71 to ST75, and hence description will not be repeated.

In the first to sixth embodiments, one angle is determined as an optimal direction. In the seventh embodiment, optimal direction candidates are calculated and presented to the operator to make him/her select a final optimal direction.

Figure 22:
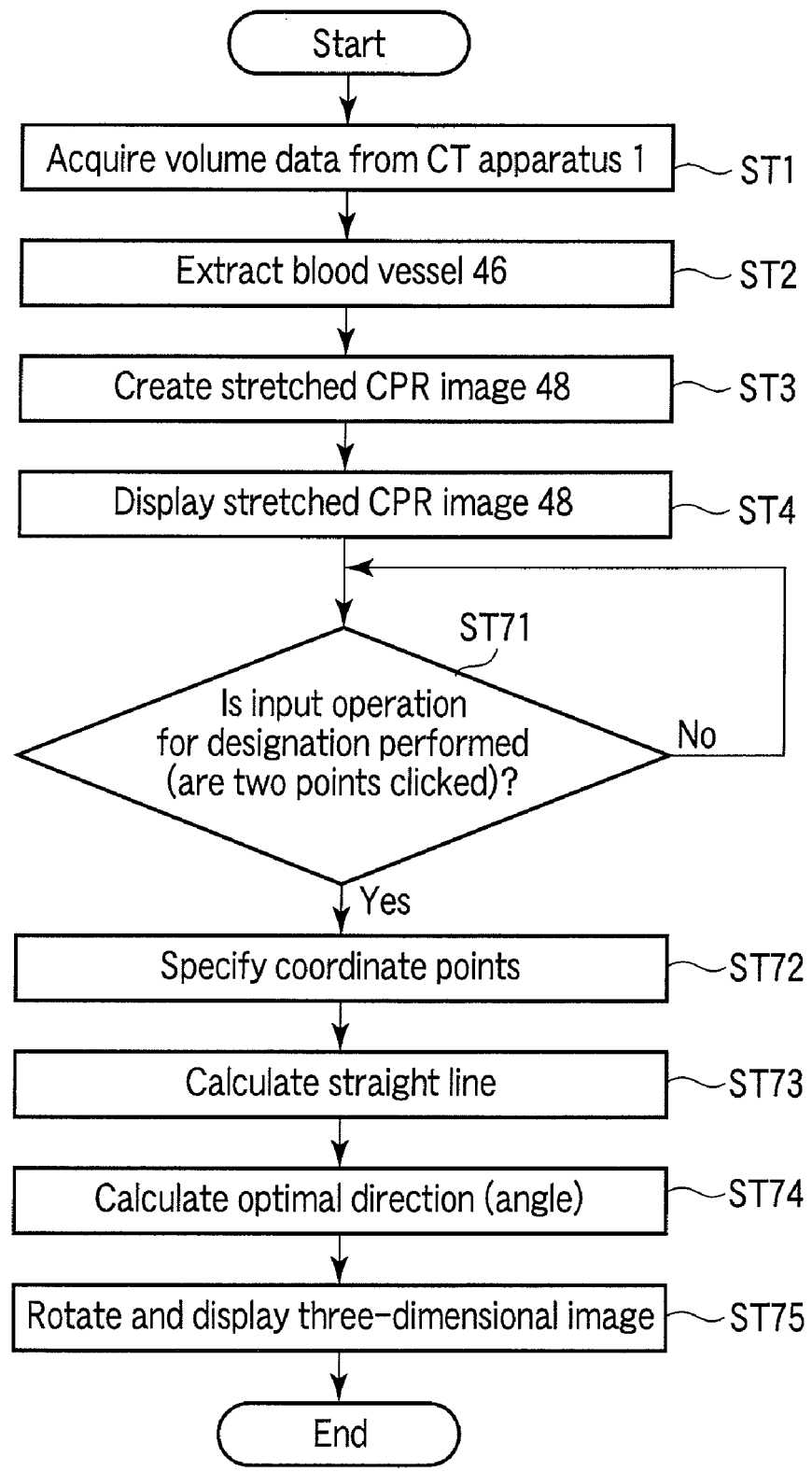
FIG. 22 is a flowchart for explaining the operation of an image display apparatus in the seventh embodiment of the present invention.
Figure 23:
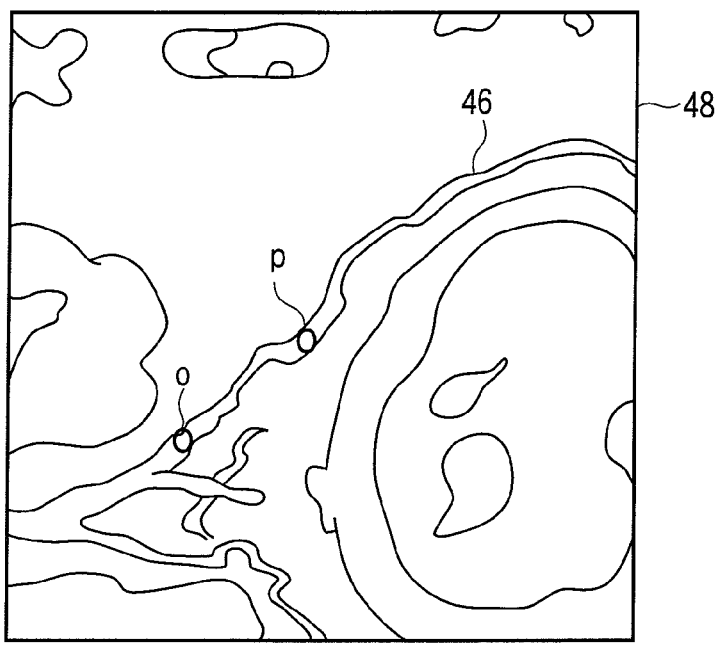
FIG. 23 is a view showing a display part and its operation sequence in the seventh embodiment.
Figure 24:
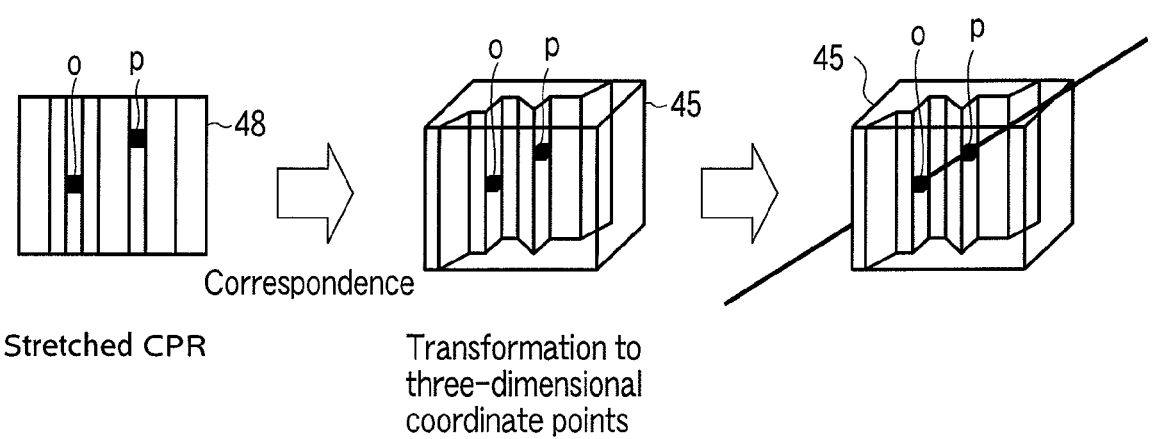
FIG. 24 is a view for explaining an operation sequence in the seventh embodiment.

In this embodiment, as shown in FIG. 22, after the processing in steps ST1 to ST4 is performed as in the first embodiment, the operator designates two desired points o and p near a morbid region (stenosis) by clicking, as shown in, for example, FIG. 23 (ST71). In step ST72, as shown in FIG. 24, the two coordinate points o and p on this two-dimensional image are specified as three-dimensional coordinate points.

Figure 25:
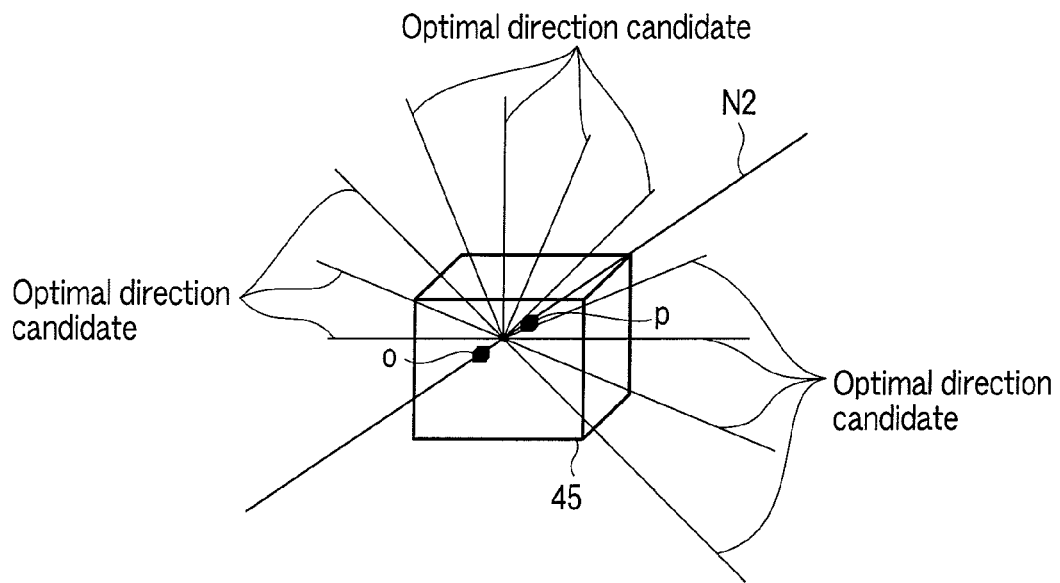
FIG. 25 is a view for explaining an operation sequence in the seventh embodiment.

As shown in FIG. 25, a straight line N2 passing through two coordinate points in this three-dimensional space is calculated (ST73). A straight line direction which is perpendicular to the straight line N2 and passes through a mid-point between the points o and p is set as an optimal direction candidate (S74).

Figure 26:
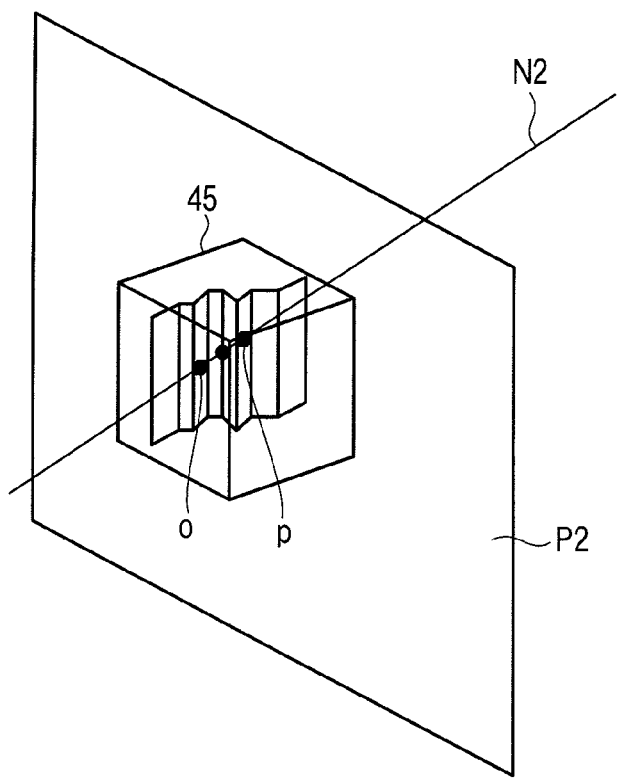
FIG. 26 is a view for explaining an operation sequence in the seventh embodiment.

In other words, as shown in FIG. 26, a plane P2 which is perpendicular to the straight line N2 and passes through a mid-point between the points o and p is assumed, and a direction seen from a viewpoint set in the plane P2 is determined as an optimal direction candidate.

Based on the calculated optimal direction candidate, a display part displays a three-dimensional image which can be rotated in the optimal direction candidate (ST75). As a display method of rotatably presenting a three-dimensional image, a method using, for example, VR or MIP images is used most frequently. Images are rotatably displayed, and angles are displayed in numbers together. The center of this rotation is the straight line N2 described above.

Other processes are the same as those in the first to sixth embodiments.

The data processing apparatus, X-ray apparatus, and data processing method according to this embodiment can obtain the same effects as those obtained by the data processing apparatus, X-ray apparatus, and data processing method according to the first to sixth embodiments.

[Eighth Embodiment]

A data processing apparatus, X-ray apparatus, and data processing method according to the eighth embodiment of the present invention will be described next with reference to FIGS. 28 and 29. Note that the data processing apparatus, X-ray apparatus, and data processing method according to this embodiment are the same as those according to the seventh embodiment except for steps ST81 to ST83, and hence description will not be repeated.

In this embodiment, as shown in FIG. 28, after the processing in steps ST1 to ST4 is performed as in the seventh embodiment, the operator designates one desired portion q near a morbid region (stenosis) by clicking, as shown in, for example, FIG. 29 (ST81). This coordinate point is specified (ST82).

In this case, a tangent to a point q is calculated by using a vascular centerline 46a which has already been extracted (ST83). This calculated tangent is set as a straight line N2 (ST73), and the same processing as in the seventh embodiment is performed.

The data processing apparatus, X-ray apparatus, and data processing method according to this embodiment can obtain the same effects as those obtained by the data processing apparatus, X-ray apparatus, and data processing method according to the first to seventh embodiments.

[Ninth Embodiment]

A data processing apparatus, X-ray apparatus, and data processing method according to the ninth embodiment of the present invention will be described next with reference to FIGS. 30 and 31. Note that the data processing apparatus, X-ray apparatus, and data processing method according to this embodiment are the same as those according to the seventh embodiment except for steps ST91 and ST92, and hence description will not be repeated.

Figure 30:
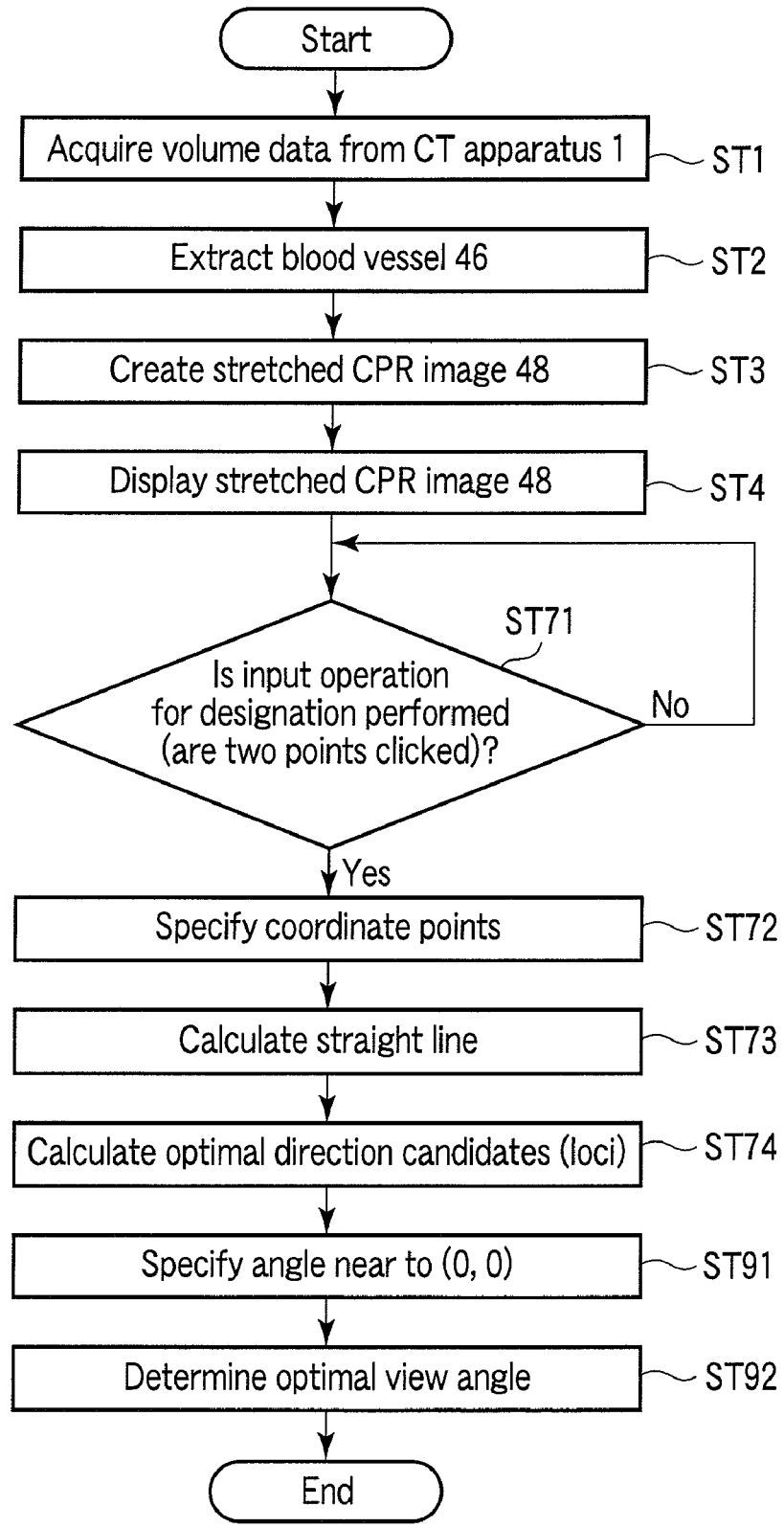
FIG. 30 is a flowchart for explaining the operation of an image display apparatus in the ninth embodiment of the present invention.

In this embodiment, as shown in FIG. 30, the processing in steps ST1 to ST74 is performed in the same manner as in the seventh embodiment, and optimal direction candidates as arcuated loci are presented while an image is rotatably displayed. Thereafter, as shown in FIGS. 30 and 31, of the optimal direction candidates, an angle nearest to the coordinate point (0, 0), i.e., CRA/CAU=0° and LAO/RAO=0°, is calculated (ST91). This calculated direction is determined as an optimal direction (ST92).

As shown in FIG. 31, the nearer to the coordinate point (0, 0), the more square the subject is imaged. When the subject is imaged square, therefore, the exposure of X-rays to the subject is minimized. This is suitable for the subject. Therefore, this angle is set as an optimal direction.

The data processing apparatus, X-ray apparatus, and data processing method according to this embodiment can obtain the same effects as those obtained by the data processing apparatus, X-ray apparatus, and data processing method according to the first to eighth embodiments.

In addition, this embodiment can minimize the exposure of X-rays to the subject, and hence is suitable for the subject.

[10th Embodiment]

A data processing apparatus, X-ray apparatus, and data processing method according to the 10th embodiment of the present invention will be described next with reference to FIG. 32. Note that the data processing apparatus, X-ray apparatus, and data processing method according to this embodiment are the same as those according to the first embodiment except for steps ST101 to ST103, and hence description will not be repeated.

Figure 32:
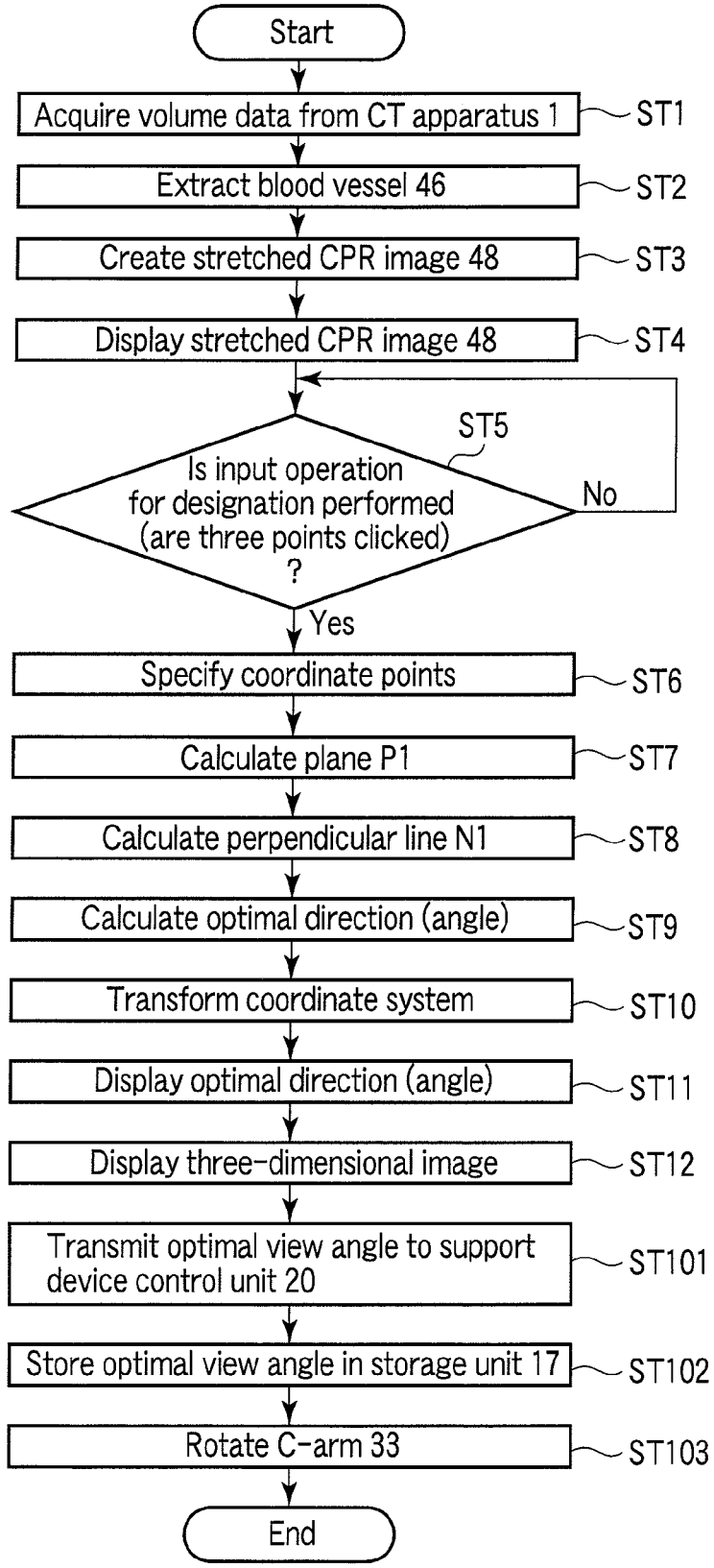
FIG. 32 is a flowchart for explaining the operation of an image display apparatus in the 10th embodiment of the present invention.

In this embodiment, as shown in FIG. 32, the processing in steps ST1 to ST12 is performed in the same manner as in the first embodiment, and an optimal direction is presented while an image is displayed.

Thereafter, the information on the determined optimal direction is sent to a support device control unit 22 (ST101). At the same time, the information on the optimal direction is temporarily stored in a storage unit 17 (ST102).

The support device control unit 22 then controls a C-arm 33 in accordance with the angle stored in the storage unit 17 to rotate the C-arm 33 so as to position it in the optimal direction (ST103).

The data processing apparatus, X-ray apparatus, and data processing method according to this embodiment can obtain the same effects as those obtained by the data processing apparatus, X-ray apparatus, and data processing method according to the first to eighth embodiments. Although the above description has exemplified a case in which the processing in steps ST101 to ST103 which is a characteristic feature of this embodiment is combined with the first embodiment, the present invention is not limited to this. This processing can be combined with any one of the first to ninth embodiments.

[11th Embodiment]

Figure 33:
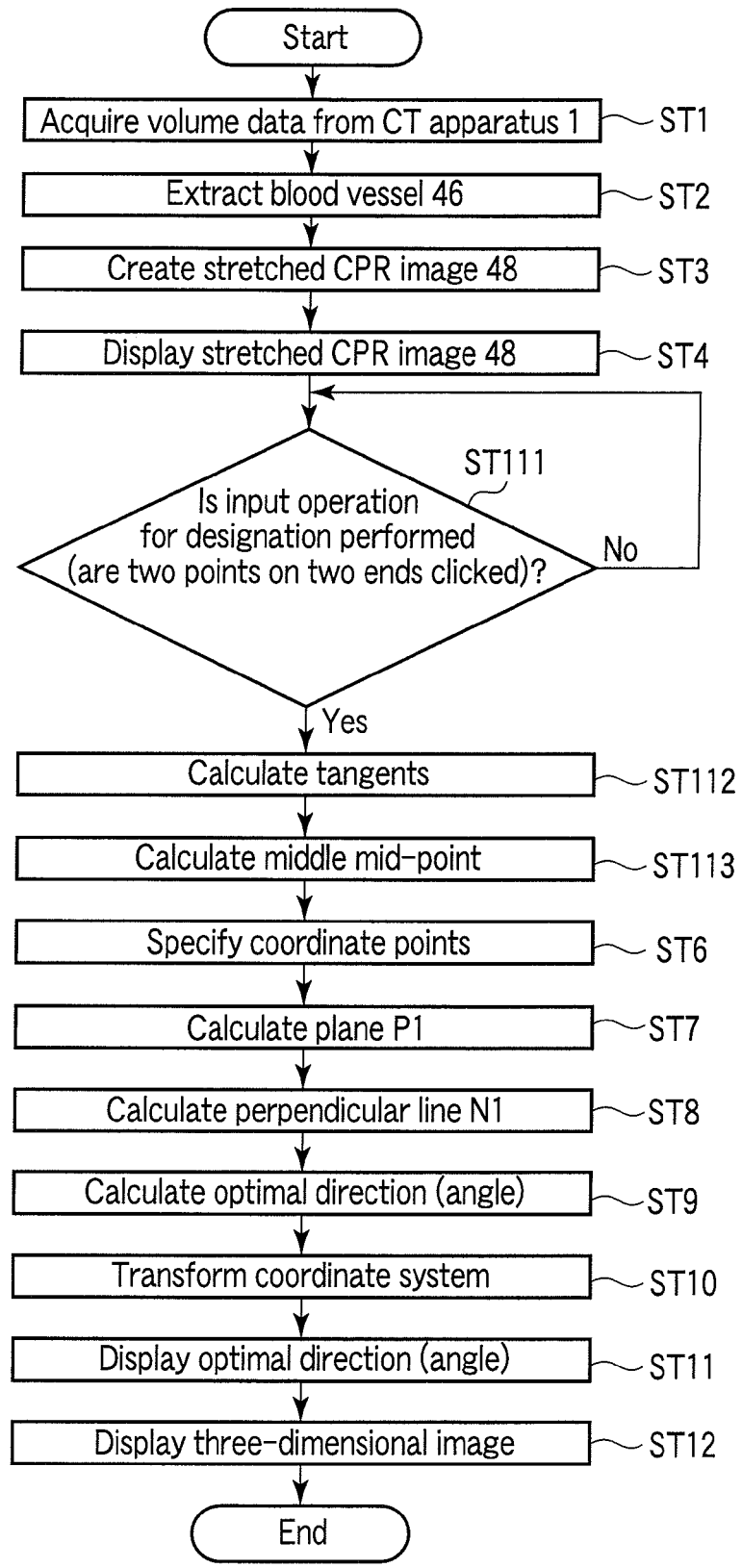
FIG. 33 is a flowchart for explaining the operation of an image display apparatus in the 11th embodiment of the present invention.

A data processing apparatus, X-ray apparatus, and data processing method according to the 11th embodiment of the present invention will be described next with reference to FIGS. 33 and 34. Note that the data processing apparatus, X-ray apparatus, and data processing method according to this embodiment are the same as those according to the first embodiment except for steps ST111 to ST113, and hence description will not be repeated.

Figure 34:
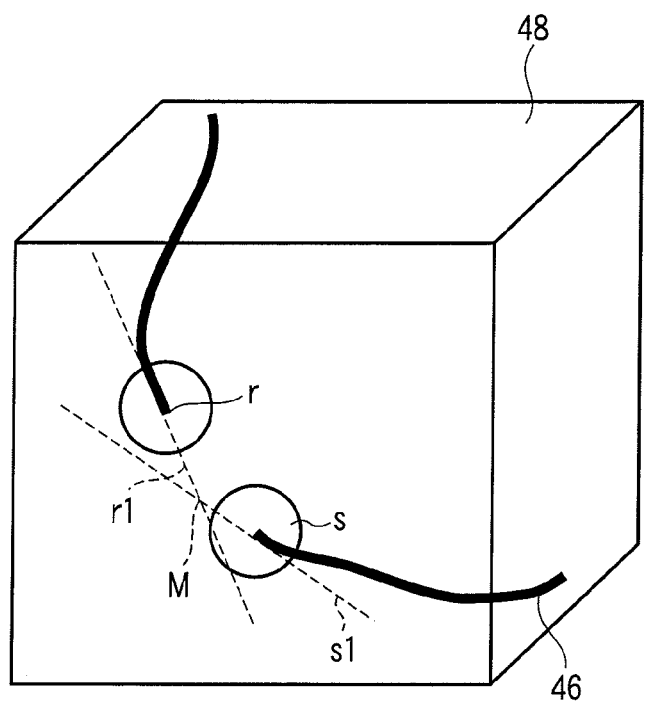
FIG. 34 is a view showing an operation sequence in the 11th embodiment.

As shown in, for example, FIG. 34, this embodiment is applied to a case of a totally occluded blood vessel (chronic total occlusion (CTO)). In this case, since a contrast agent does not flow in an occluded portion, the occluded portion is not imaged, and a vascular centerline 46a is disconnected. In this case, the operator designates two ends r and s of the blood vessel of the occluded portion by clicking operation or the like (ST111). In this case, it is determined that the vascular centerline 46a of a blood vessel 46 is not continuous (ST112). Tangents l1 and l2 to the two designated ends of the vascular centerline are calculated (ST113). A mid-point M at which the distance between tangents r1 and s1 is minimized is calculated. A plane P1 passing through the three points, i.e., the mid-point M obtained in this manner and the two designated points r and s, is obtained, and the same processing as that in the first embodiment is performed.

The data processing apparatus, X-ray apparatus, and data processing method according to this embodiment can obtain the same effects as those obtained by the data processing apparatus, X-ray apparatus, and data processing method according to the first embodiment. Although the above description has exemplified a case in which the processing in steps ST111 to ST113 which is a characteristic feature of this embodiment is combined with the first embodiment, the present invention is not limited to this. This processing can be combined with any one of the first to 10th embodiments.

[12th Embodiment]

Figure 36:
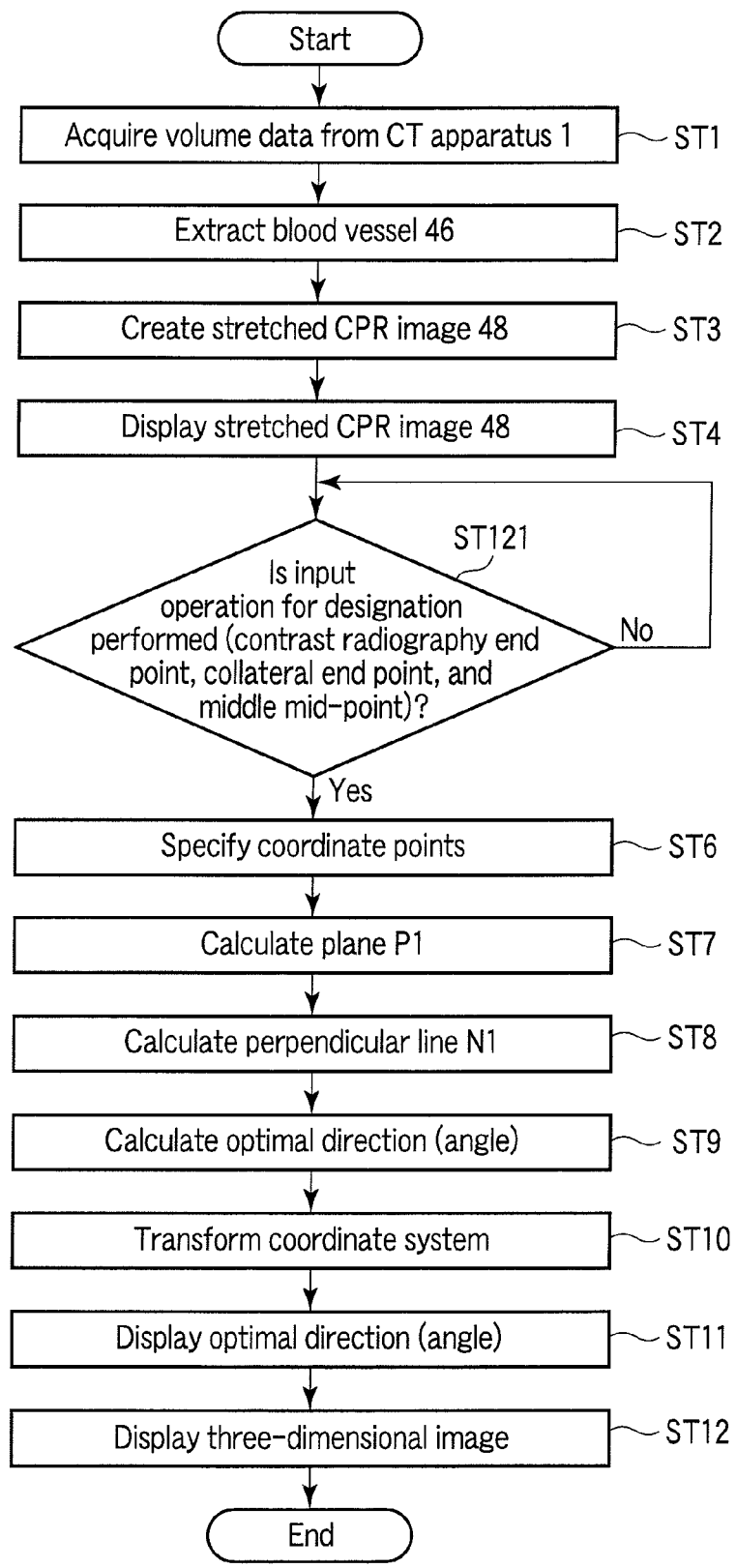
FIG. 36 is a flowchart for explaining the operation of an image display apparatus in the 12th embodiment.
Figure 37:
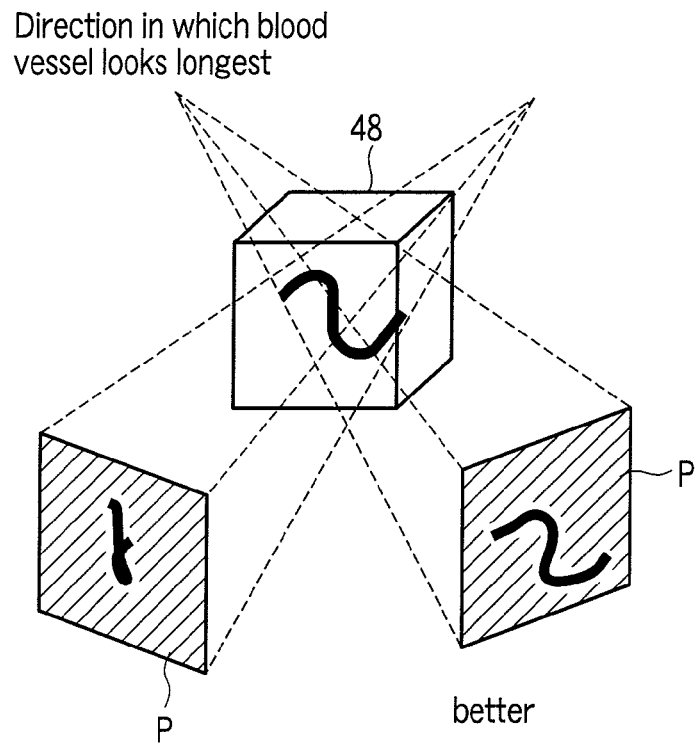
FIG. 37 is a view showing an operation sequence in the 12th embodiment.

A data processing apparatus, X-ray apparatus, and data processing method according to the 12th embodiment of the present invention will be described next with reference to FIGS. 35 to 37. Note that the data processing apparatus, X-ray apparatus, and data processing method according to this embodiment are the same as those according to the first embodiment except for step ST121, and hence description will not be repeated.

Figure 35:
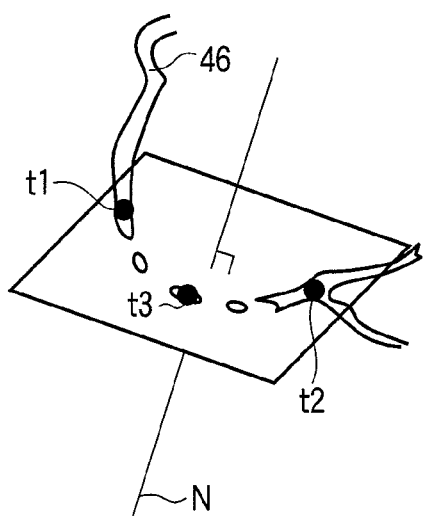
FIG. 35 is a view showing an operation sequence in the 12th embodiment of the present invention.

As shown in, for example, FIG. 35, this embodiment is applied to a case of a totally occluded blood vessel. In this case, since a contrast agent does not flow in an occluded portion, the occluded portion is not imaged, and a vascular centerline 46a is disconnected. In this case, as shown in FIGS. 35 and 37, the operator designates a contrast radiography end point t1, a collateral end point t2, and a mid-point t3 by clicking operation or the like (ST121). A plane P1 passing through the three points obtained by this operation is obtained, and the same processing as that in the first embodiment is performed. With the above processing, as shown in FIG. 37, an optimal direction in which the morbid region looks longest can be found.

The data processing apparatus, X-ray apparatus, and data processing method according to this embodiment can obtain the same effects as those obtained by the data processing apparatus, X-ray apparatus, and data processing method according to the first embodiment. Although the above description has exemplified a case in which the processing in step ST121 which is a characteristic feature of this embodiment is combined with the first embodiment, the present invention is not limited to this. This processing can be combined with any one of the first to 11th embodiments.

[13th Embodiment]

A data processing apparatus, X-ray apparatus, and data processing method according to the 13th embodiment of the present invention will be described next with reference to FIGS. 38 to 40. Note that the data processing apparatus, X-ray apparatus, and data processing method according to this embodiment are the same as those according to the first embodiment except for step ST131, and hence description will not be repeated.

Figure 38:
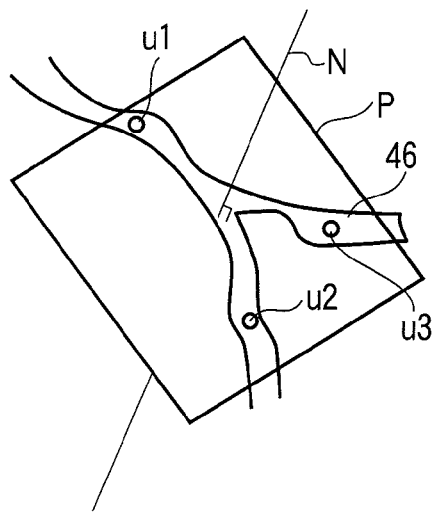
FIG. 38 is a view for explaining an operation sequence in the 12th embodiment of the present invention.
Figure 39:
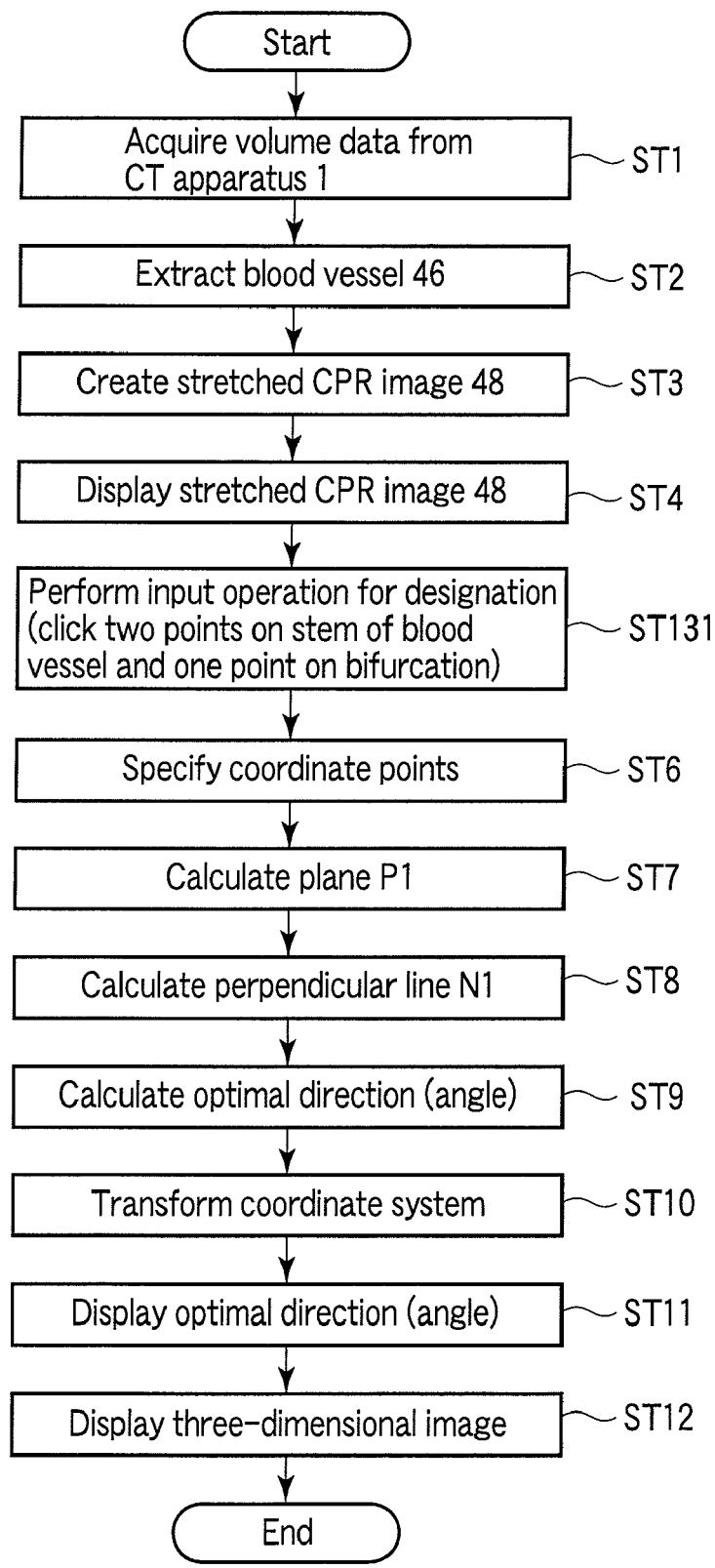
FIG. 39 is a flowchart for explaining the operation of an image display apparatus in the 12th embodiment.

As shown in, for example, FIG. 38, this embodiment is applied to a case in which a target blood vessel bifurcates. In this case, as shown in FIGS. 38 and 39, the operator designates two points u1 and u2 on the stem of the blood vessel and one point u3 on the bifurcated portion by clicking operation or the like (ST131). A plane P1 passing through the three points obtained by this operation is obtained, and the same processing as that in the first embodiment is performed. With the above processing, as shown in FIG. 40, an optimal direction in which the bifurcation looks widest, and the morbid region can be seen most clearly can be found.

The data processing apparatus, X-ray apparatus, and data processing method according to this embodiment can obtain the same effects as those obtained by the data processing apparatus, X-ray apparatus, and data processing method according to the first embodiment. Although the above description has exemplified a case in which the processing in step ST131 which is a characteristic feature of this embodiment is combined with the first embodiment, the present invention is not limited to this. This processing can be combined with any one of the first to 12th embodiments.

Although the embodiments of the present invention have been described, the present invention is not limited to these embodiments. The embodiments can be variously modified and changed within the spirit and scope of the invention.

Although the above description has exemplified the volume data of a blood vessel obtained by CT, the target to be imaged in the present invention is not limited to a blood vessel. For example, the present invention can be applied to a bone, a hollow organ (small intestine, large intestine, or the like), an implanted device such as a stent or graft, and the like. The present invention is not limited to the data captured by the CT apparatus, and can also use the data captured by other apparatuses such as an X-ray apparatus, MRI apparatus, and ultrasonic apparatus.

Furthermore, the present invention is not limited to CT volume data and can be applied to any data as long as it is 3D data such as MRI data and PET data. The types of data to which the present invention can be applied also include, for example, vessel tree data.

In addition, the above description has exemplified a stretched CPR image as an initial image. However, the present invention is not limited to this, and can use a straightened CPR image or can use an MPR image as shown in, for example, FIG. 41. Assume that a plurality of MPR images 51 and 52 are used. In this case, one point 51a designated on one MPR image 51 provides one point in a three-dimensional space 50, and one point 52a designated on another MPR image 52 provides another point in the same three-dimensional space 50. If two or more points in a corresponding three-dimensional space can be obtained in this manner, the same technique as that used for the above CPR image can be used unchanged. If only one point is designated, another point can be determined in the same manner as in the second embodiment.

In addition, the above embodiments use, as a two-dimensional image, a CPR image of a right section which is cut in the same direction so as to pass through an arbitrary curve in the volume data of a three-dimensional image. However, the present invention is not limited to this. For example, as disclosed in Jpn. Pat. Appln. KOKAI Publication No. 2006-122663, a CPR image of a curved section can be used.

Furthermore, it suffices to selectively use the determination methods based on a plurality of embodiments. For example, it suffices to include the step of determining the shape of a vascular centerline 46a and the step of selecting one of the optimal direction determining methods in the first to the 13th embodiments and calculate an optimal direction by using the selected preferable determination method. If, for example, a vascular centerline extends linearly, a direction in which the straight line looks long is determined as an optimal direction. If the vascular centerline of a designated portion bifurcates, a direction in which a bifurcation angle looks widest is determined as an optimal direction.

The above embodiments include inventions of various stages, and various inventions can be extracted by proper combinations of a plurality of disclosed constituent elements. When, for example, the problems described in "Description of the Related Art" can be solved and the effects described in "BRIEF SUMMARY OF THE INVENTION" can be obtained even if several constituent elements are omitted from all the constituent elements in each embodiment, the arrangement from which these constituent elements are omitted can be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A data processing apparatus comprising:
    a saving part configured to save three-dimensional data of a subject;
    a two-dimensional image display part configured to display three-dimensional data of the subject as a two-dimensional image;
    a designation part configured to designate coordinate information associated with a specific coordinate point on the two-dimensional image;
    a specifying part configured to specify, based on the coordinate information designated on the two-dimensional image, coordinate information on the corresponding three-dimensional data; and
    a calculation part configured to calculate a view angle of the subject on the basis of the coordinate information on the three-dimensional data, the coordinate information being designated as not less than one point, not less than one region, or not less than one line on the image, and the calculation part defining a plane in a space on the basis of the coordinate information, and setting a direction perpendicular to the plane as the view angle.

2. The apparatus according to claim 1, wherein the three-dimensional data comprises data which is captured by one of an X-ray apparatus, a CT apparatus, an MRI apparatus, an ultrasonic apparatus, and a PET apparatus and three-dimensionally converted.

3. The apparatus according to claim 1, wherein the two-dimensional image display part displays a pixel corresponding to a voxel of the three-dimensional data as two-dimensional data.

4. The apparatus according to claim 1, wherein when three points are designated, the calculation part calculates, as the plane, a plane passing through the specified three points.

5. The apparatus according to claim 1, wherein when not less than four points, a line, or a region is designated, the calculation part calculates, as the plane, a plane which passes through three points of the points, the line, or the region and minimizes a distance to a designated point.

6. The apparatus according to claim 1, wherein when two points are designated, the calculation part calculates, as the plane, a plane passing through the two points and a mid-point therebetween.

7. The apparatus according to claim 1, wherein when one point is designated, the calculation part calculates, as the plane, a plane passing through the point and points which are located before and after the point and spaced apart therefrom by a predetermined distance.

8. The apparatus according to claim 1, wherein when there is a disconnected portion on the two-dimensional image in which an imaging target is disconnected, the calculation part designates two ends of the disconnected portion, and calculates, as the plane, a plane passing between tangents to the two ends and points at the two ends.

9. The apparatus according to claim 1, wherein when there is a bifurcated portion on the two-dimensional image in which an imaging target bifurcates, the calculation part calculates, as the view angle, a direction in which an angle of the bifurcated portion looks largest.

10. The apparatus according to claim 1, which further comprises an input part, configured to select an imaging target region as selection information, for inputting desired selection information for the two-dimensional image, and in which
    the selected target region is extracted and displayed on the two-dimensional image display part.

11. The apparatus according to claim 1, further comprising a three-dimensional display part configured to display the three-dimensional image in a direction in which the image is projected at a view angle calculated by the calculation part.

12. The apparatus according to claim 1, wherein the view angle satisfies predetermined conditions including movement of an X-ray apparatus.

13. The apparatus according to claim 1, wherein the two-dimensional image comprises a curved MPR image.

14. The apparatus according to claim 1, further comprising:
    a X-ray generating part configured to apply X-rays to the subject;
    a X-ray detection part configured to detect X-rays applied from the X-ray generating part;
    a moving part configured to move the X-ray generating part and the X-ray detection part; and
    a movement control part configured to control movement of the moving part on the basis of the calculated view angle.

15. A data processing method comprising steps of:
    displaying three-dimensional data of a subject as a two-dimensional image;
    designating coordinate information associated with a specific coordinate point on the two-dimensional image;
    specifying, based on the coordinate information designated on the two-dimensional image, coordinate information on the corresponding three-dimensional data; and
    calculating a view angle of the subject on the basis of the coordinate information on the three-dimensional data, the coordinate information being designated as not less than one point, not less than one region, or not less than one line on the image, and the calculation part defining a plane in a space on the basis of the coordinate information, and setting a direction perpendicular to the plane as the view angle.

* * * * *